United States Patent
Aebi et al.

(10) Patent No.: US 9,464,058 B2
(45) Date of Patent: Oct. 11, 2016

(54) IMIDAZOLYLKETONE DERIVATIVES

(71) Applicant: Hoffmann-La Roche Inc., Nutley, NJ (US)

(72) Inventors: Johannes Aebi, Binningen (CH); Kurt Amrein, Itingen (CH); Benoit Hornsperger, Altkirch (FR); Bernd Kuhn, Reinach BL (CH); Hans P. Maerki, Basel (CH); Alexander V. Mayweg, Basel (CH); Peter Mohr, Basel (CH); Xuefei Tan, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 13/766,010

(22) Filed: Feb. 13, 2013

(65) Prior Publication Data
US 2014/0128429 A1    May 8, 2014

Related U.S. Application Data

(63) Continuation of application No. PCT/CN2012/071064, filed on Feb. 13, 2012.

(51) Int. Cl.
| C07D 233/64 | (2006.01) |
| C07D 409/06 | (2006.01) |
| C07D 401/06 | (2006.01) |

(52) U.S. Cl.
CPC ........... *C07D 233/64* (2013.01); *C07D 401/06* (2013.01); *C07D 409/06* (2013.01)

(58) Field of Classification Search
CPC . C07D 233/64; C07D 409/06; C07D 401/06
See application file for complete search history.

(56) References Cited

U.S. PATENT DOCUMENTS 7,253,183 B2 *   8/2007   End et al. .................. 514/312
2003/0087940 A1 *   5/2003   Claiborne et al. ............ 514/365

FOREIGN PATENT DOCUMENTS

JP    63239273 A  * 10/1988
JP    07033374 B  *  4/1995

OTHER PUBLICATIONS

Kihara et al. "Phenylimidazoles for treatment of cerebral disorders, amnesia, and senile dementia." JP 07-033374 B Apr. 12, 1995 (equivalent of 63239273A), English machine translation.*

* cited by examiner

*Primary Examiner* — Nyeemah A Grazier
*Assistant Examiner* — Amanda L Aguirre
(74) *Attorney, Agent, or Firm* — Robert C. Hall

(57) ABSTRACT

The invention provides novel compounds having the general formula (I)

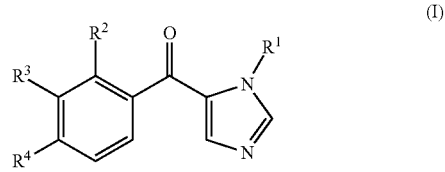

wherein $R^1$, $R^2$, $R^3$ and $R^4$ n are as described herein, compositions including the compounds and methods of using the compounds.

17 Claims, No Drawings

IMIDAZOLYLKETONE DERIVATIVES

CROSS REFERENCE TO RELATED APPLICATIONS

This application claims priority under 35 USC §120, or alternatively under 35 USC §119, to Application PCT/CN2012/071064 filed in China on Feb. 13, 2012, the disclosure of which is incorporated herein by reference.

FIELD OF THE INVENTION

The present invention relates to organic compounds useful for therapy or prophylaxis in a mammal, and in particular to aldosterone synthase (CYP11B2 or CYP11B1) inhibitors for the treatment or prophylaxis of chronic kidney disease, congestive heart failure, hypertension, primary aldosteronism and Cushing syndrome.

BACKGROUND OF THE INVENTION

Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically, aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

There is ample preclinical evidence that MR-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt diet and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, led to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate various CYP11B2 inhibitors.

SUMMARY OF THE INVENTION

The present invention provides novel compounds of formula (I)

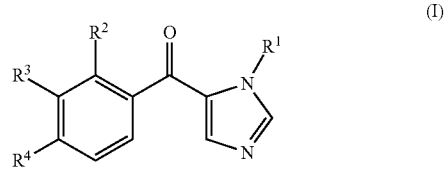

wherein
$R^1$ is alkyl, haloalkyl, cycloalkyl, halocycloalkyl, cycloalkylalkyl, halocycloalkylalkyl, alkoxyalkyl, haloalkoxyalkyl, hydroxyalkyl, substituted aryl or substituted heteroaryl, wherein substituted aryl and substituted heteroaryl are substituted with $R^5$, $R^6$ and $R^7$;

$R^2$ is H, halogen, cyano, nitro, alkyl, haloalkyl, cycloalkyl, halocycloalkyl, cycloalkylalkyl, halocycloalkylalkyl, alkoxy, haloalkoxy, alkoxyalkyl, haloalkoxyalkyl, cycloalkoxy, halocycloalkoxy or hydroxyalkyl;

$R^3$ is H, halogen, cyano, nitro, alkyl, haloalkyl, cycloalkyl, halocycloalkyl, cycloalkylalkyl, halocycloalkylalkyl, alkoxy, haloalkoxy, alkoxyalkyl, haloalkoxyalkyl, cycloalkoxy, halocycloalkoxy or hydroxyalkyl;

$R^4$ is H, halogen, cyano, nitro, substituted amino, alkyl, cycloalkyl, halocycloalkyl, cycloalkylalkyl, halocycloalkylalkyl, alkynyl, alkoxy, haloalkoxy, alkylsulfanyl, cycloalkylsulfanyl, haloalkylsulfanyl, alkylsulfonyl, cycloalkylsulfonyl, haloalkylsulfonyl, alkoxyalkyl, haloalkoxyalkyl, cycloalkoxy, halocycloalkoxy or hydroxyalkyl, wherein substituted amino is substituted with $R^8$ and $R^9$;

or $R^3$ and $R^4$ together form —CH$_2$—CH$_2$—C(O)—N(CH$_3$)— or —CH=CH—S—

$R^5$, $R^6$ and $R^7$ are independently selected from H, halogen, cyano, alkyl, haloalkyl, cycloalkyl, halocycloalkyl, cycloalkylalkyl, halocycloalkylalkyl, alkoxy, haloalkoxy, alkoxyalkyl, haloalkoxyalkyl, cycloalkoxy, halocycloalkoxy and hydroxyalkyl;

$R^8$ is alkyl, cycloalkyl, formyl, alkylcarbonyl or alkoxycarbonyl;

$R^9$ is H, alkyl or cycloalkyl;

or pharmaceutically acceptable salts;

with the proviso that at least one of $R^2$, $R^3$ and $R^4$ is different from H and that CAS 213389-81-2; CAS 222978-28-1; CAS 443920-37-4; CAS 371765-82-1; CAS 280143-24-0; CAS 192187-41-0; CAS 1227383-33-6; CAS 1227383-32-5; CAS 1227383-30-3; CAS 1227383-28-9; CAS 1118761-69-5; CAS 1050749-75-1; CAS 1283718-66-0; CAS 491867-48-2 and CAS 942836-16-0 are excluded.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrome, and the use of the said compounds, salts or esters for the production of medicaments for the treatment or prophylaxis of chronic kidney disease, congestive heart failure, hypertension, primary aldosteronism and Cushing syndrome.

DETAILED DESCRIPTION OF THE INVENTION

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl group include methoxymethyl, methoxyethyl and isopropoxymethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy, ethoxy, n-propoxy, isopropoxy, n-butoxy, isobutoxy and tert-butoxy. Particular alkoxycarbonyl group is a group of the formula —C(O)—R', wherein R' is tert-butoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl and sec-butyl, pentanyl. Particular alkyl groups include methyl, ethyl, propyl, isopropyl, sec-butyl and pentan-3-yl. More particular alkyl groups are methyl, ethyl, isopropyl and pentan-3-yl.

The term "alkylcarbonyl" denotes a group of the formula —C(O)—R', wherein R' is an alkyl group. Examples of alkylcarbonyl groups include groups of the formula —C(O)—R', wherein R' is methyl or ethyl. Particular alkylcarbonyl groups include groups of the formula —C(O)—R', wherein R' is methyl.

The term "alkylsulfanyl" denotes a group of the formula —S—R', wherein R' is an alkyl group. Examples of alkylsulfanyl groups include groups of the formula —S—R', wherein R' is methyl, ethyl, n-propyl, isopropyl, n-butyl, isobutyl or tert-butyl. Particular alkylsulfanyl groups include groups of the formula —S—R', wherein R' is methyl or ethyl.

The term "alkylsulfonyl" denotes a group of the formula —S(O)$_2$—R', wherein R' is an alkyl group. Examples of alkylsulfonyl groups include groups of the formula —S(O)$_2$—R', wherein R' is methyl, ethyl, n-propyl, isopropyl, n-butyl, isobutyl or tert-butyl. Particulars alkylsulfonyl groups include groups of the formula —S(O)$_2$—R', wherein R' is methyl or ethyl.

The term "alkynyl" denotes a monovalent linear or branched saturated hydrocarbon group of 2 to 7 carbon atoms comprising one, two or three triple bonds. In particular embodiments, alkynyl has from 2 to 4 carbon atoms comprising one or two triple bonds. Examples of alkynyl include ethynyl, propynyl, prop-2-ynyl, isopropynyl, n-butynyl, and iso-butynyl. Particular alkynyl is ethynyl.

The term "amino" denotes a —NH$_2$ group.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carbonyl" denotes a —C(O)— group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means consisting of two saturated carbocycles having two carbon atoms in common Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl and cyclopentylbutyl. Particular examples of cycloalkylalkyl groups are cyclopropylmethyl, cyclopropylbutyl and 2-cyclopropylbutyl.

The term "cycloalkylsulfanyl" denotes a group of the formula —S—R', wherein R' is a cycloalkyl group. Examples of cycloalkylsulfanyl groups include groups of the formula —S—R', wherein R' is cyclopropyl.

The term "cycloalkylsulfonyl" denotes a group of the formula —S(O)$_2$—R', wherein R' is a cycloalkyl group. Examples of cycloalkylsulfonyl groups include groups of the formula —S(O)$_2$—R', wherein R' is cyclopropyl.

The term "formyl" denotes a —CH(O) group.

The term "haloalkoxy" denotes an alkoxy group wherein at least one of the hydrogen atoms of the alkoxy group has been replaced by the same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and 2,2,2-trifluoroethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl is 2,2,2-trifluoroethoxyethyl.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "haloalkylsulfanyl" denotes a group of the formula —S—R', wherein R' is a haloalkyl group. Examples of haloalkylsulfanyl groups include groups of the formula —S—R', wherein R' is fluoromethyl, difluoromethyl, trifluoromethyl, trifluoroethyl, trifluoromethylethyl or pentafluoroethyl. Particular haloalkylsulfanyl groups include groups of the formula —S—R', wherein R' is trifluoromethyl.

The term "haloalkylsulfonyl" denotes a group of the formula —S(O)$_2$—R', wherein R' is a haloalkyl group. Examples of haloalkylsulfonyl groups include groups of the formula —S(O)$_2$—R', wherein R' is fluoromethyl, difluoromethyl, trifluoromethyl, trifluoroethyl, trifluoromethylethyl or pentafluoroethyl. Particulars haloalkylsulfonyl groups include groups of the formula —S(O)$_2$—R', wherein R' is trifluoromethyl.

The term "halocycloalkoxy" denotes a cycloalkoxy group wherein at least one of the hydrogen atoms of the cycloalkoxy group has been replaced by the same or different halogen atoms, particularly fluoro atoms. Examples of halocycloalkoxy groups include fluorocyclopropoxy, difluorocyclopropoxy, fluorocyclobutoxy and difluorocyclobutoxy.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halocycloalkylalkyl" denotes an alkyl group wherein at least one of the hydrogen atoms of the alkyl group has been replaced by a halocycloalkyl. Examples of halocycloalkylalkyl groups include fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl and difluorocyclobutylethyl.

The term "halogen" and "halo" are used interchangeably herein and denote fluoro, chloro, bromo, or iodo. Particular halogens are chloro and fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyrrolyl, pyrazolyl, imidazolyl, triazolyl, benzoimidazolyl, indazolyl, indolyl, pyridinyl, isooxazolyl and oxazolyl.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxy-1-methyl-ethyl, hydroxypropyl, hydroxymethylpropyl and dihydroxypropyl. Particular examples are hydroxymethyl and hydroxyethyl.

The term "nitro" denotes a —NO$_2$ group.

CAS 213389-81-2 is (4-chlorophenyl)(1-methyl-1H-imidazol-5-yl)-methanone.

CAS 222978-28-1 is 2-fluoro-4-[(1-methyl-1H-imidazol-5-yl)carbonyl]-methanone.

CAS 443920-37-4 is 4-[(1-methyl-1H-imidazol-5-yl)carbonyl]-benzonitrile.

CAS 371765-82-1 is 2-bromo-4-[(1-methyl-1H-imidazol-5-yl)carbonyl]-benzonitrile.

CAS 280143-24-0 is (4-chlorophenyl)[1-(1-methylethyl)-1H-imidazol-5-yl]-methanone.

CAS 192187-41-0 is (1-butyl-1H-imidazol-5-yl)(4-chlorophenyl)-methanone.

CAS 1227383-33-6 is [4-(1-methylethyl)phenyl](1-methyl-1H-imidazol-5-yl)-methanone.

CAS 1227383-32-5 is (4-ethylphenyl)(1-methyl-1H-imidazol-5-yl)-methanone.

CAS 1227383-30-3 is (1-methyl-1H-imidazol-5-yl)(4-methylphenyl)-methanone.

CAS 1227383-28-9 is (4-chlorophenyl)(1-ethyl-1H-imidazol-5-yl)-methanone.

CAS 1118761-69-5 is (4-chloro-3-methylphenyl)(1-methyl-1H-imidazol-5-yl)methanone.

CAS 1050749-75-1 is (1-methyl-1H-imidazol-5-yl)[3-(trifluoromethyl)phenyl]-methanone.

CAS 1283718-66-0 is (4-chloro-2-fluoro-5-methoxyphenyl)(1-methyl-1H-imidazol-5-yl)-methanone.

CAS 491867-48-2 is (2-fluorophenyl)(1-methyl-1H-imidazol-5-yl)-methanone.

CAS 942836-16-0 is (3-bromophenyl)(1-methyl-1H-imidazol-5-yl)-methanone.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol μM.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

The present invention provides a compound of formula (I)

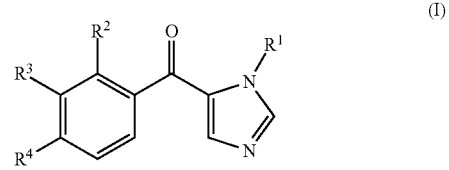

wherein
$R^1$ is alkyl, haloalkyl, cycloalkyl, halocycloalkyl, cycloalkylalkyl, halocycloalkylalkyl, alkoxyalkyl, haloalkoxyalkyl, hydroxyalkyl, substituted aryl or substituted heteroaryl, wherein substituted aryl and substituted heteroaryl are substituted with $R^5$, $R^6$ and $R^7$;

$R^2$ is H, halogen, cyano, nitro, alkyl, haloalkyl, cycloalkyl, halocycloalkyl, cycloalkylalkyl, halocycloalkylalkyl, alkoxy, haloalkoxy, alkoxyalkyl, haloalkoxyalkyl, cycloalkoxy, halocycloalkoxy or hydroxyalkyl;

$R^3$ is H, halogen, cyano, nitro, alkyl, haloalkyl, cycloalkyl, halocycloalkyl, cycloalkylalkyl, halocycloalkylalkyl, alkoxy, haloalkoxy, alkoxyalkyl, haloalkoxyalkyl, cycloalkoxy, halocycloalkoxy or hydroxyalkyl;

$R^4$ is H, halogen, cyano, nitro, substituted amino, alkyl, cycloalkyl, halocycloalkyl, cycloalkylalkyl, halocycloalkylalkyl, alkynyl, alkoxy, haloalkoxy, alkylsulfanyl, cycloalkylsulfanyl, haloalkylsulfanyl, alkylsulfonyl, cycloalkylsulfonyl, haloalkylsulfonyl, alkoxyalkyl, haloalkoxyalkyl, cycloalkoxy, halocycloalkoxy or hydroxyalkyl, wherein substituted amino is substituted with $R^8$ and $R^9$;

or $R^3$ and $R^4$ together form —$CH_2$—$CH_2$—C(O)—N($CH_3$)— or —CH=CH—S—

$R^5$, $R^6$ and $R^7$ are independently selected from H, halogen, cyano, alkyl, haloalkyl, cycloalkyl, halocycloalkyl, cycloalkylalkyl, halocycloalkylalkyl, alkoxy, haloalkoxy, alkoxyalkyl, haloalkoxyalkyl, cycloalkoxy, halocycloalkoxy and hydroxyalkyl;

$R^8$ is alkyl, cycloalkyl, formyl, alkylcarbonyl or alkoxycarbonyl;

$R^9$ is H, alkyl or cycloalkyl;

or pharmaceutically acceptable salts;

with the proviso that at least one of $R^2$, $R^3$ and $R^4$ is different from H, and that the compound is not CAS 213389-81-2; CAS 222978-28-1; CAS 443920-37-4; CAS 371765-82-1; CAS 280143-24-0; CAS 192187-41-0; CAS 1227383-33-6; CAS 1227383-32-5; CAS 1227383-30-3; CAS 1227383-28-9; CAS 1118761-69-5; CAS 1050749-75-1; CAS 1283718-66-0; CAS 491867-48-2 or CAS 942836-16-0.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A further embodiment of the present invention are compounds according to formula (I) as described herein, wherein $R^1$ is alkyl, haloalkyl, cycloalkyl or substituted aryl, wherein substituted aryl is substituted with $R^5$, $R^6$ and $R^7$.

A particular embodiment of the present invention are compounds according to formula (I) as described herein, wherein $R^1$ is alkyl, haloalkyl, cycloalkyl or substituted phenyl, wherein substituted phenyl is substituted with $R^5$, $R^6$ and $R^7$.

In a further embodiment of the present invention are compounds according to formula (I) as described herein, wherein $R^1$ is alkyl, haloalkyl, cycloalkyl or substituted phenyl, wherein substituted phenyl is substituted with one to three substituents independently selected from halogen and cyano.

Another further embodiment of the present invention are compounds according to formula (I) as described herein, wherein $R^1$ is alkyl, haloalkyl, cycloalkyl, chlorophenyl, cyanophenyl or chlorocyanophenyl.

Another embodiment of the present invention are compounds according to formula (I) as described herein, wherein $R^1$ is alkyl or substituted aryl, wherein substituted aryl is substituted with $R^5$, $R^6$ and $R^7$.

The present invention also relates to compounds according to formula (I) as described herein, wherein $R^1$ is methyl, ethyl, isopropyl, pentan-3-yl or cyanophenyl.

A further particular embodiment of the present invention are compounds according to formula (I) as described herein, wherein $R^2$ is H or halogen.

A more particular embodiment of the present invention are compounds according to formula (I) as described herein, wherein $R^2$ is H, chloro or fluoro.

Also an embodiment of the present invention are compounds according to formula (I) as described herein, wherein $R^2$ is H.

The present invention also relates to compounds according to formula (I) as described herein, wherein $R^3$ is H, halogen, cyano or alkoxy.

Another embodiment of the present invention are compounds according to formula (I) as described herein, wherein $R^3$ is H, chloro, fluoro, cyano or methoxy.

A further particular embodiment of the present invention are compounds according to formula (I) as described herein, wherein is $R^3$ is H, chloro or methoxy.

A particular embodiment of the present invention are compounds according to formula (I) as described herein, wherein $R^4$ is H, halogen, cyano, substituted amino, alkyl, alkynyl, alkoxy, alkylsulfanyl, haloalkylsulfanyl or alkylsulfonyl, wherein substituted amino is substituted with $R^8$ and $R^9$.

Also an embodiment of the present invention are compounds according to formula (I) as described herein, wherein $R^4$ is halogen, cyano, substituted amino or alkylsulfanyl, wherein substituted amino is substituted with formyl and alkyl.

The present invention also relates to compounds according to formula (I) as described herein, wherein $R^3$ and $R^4$ together form —CH$_2$—CH$_2$—C(O)—N(CH$_3$)— or —CH=CH—S—.

Another embodiment of the present invention are compounds according to formula (I) as described herein, wherein $R^3$ and $R^4$ together form —CH$_2$—CH$_2$—C(O)—N(CH$_3$)—.

The present invention also relates to compounds according to formula (I) as described herein, wherein $R^5$, $R^6$ and $R^7$ are independently selected from H, halogen or cyano.

Also an embodiment of the present invention are compounds according to formula (I) as described herein, wherein $R^5$, $R^6$ and $R^7$ are independently selected from H, halogen or cyano.

Another embodiment of the present invention are compounds according to formula (I) as described herein, wherein $R^5$, $R^6$ and $R^7$ are independently selected from H or cyano.

Also an embodiment of the present invention are compounds according to formula (I) as described herein, wherein $R^8$ is alkyl, formyl, alkylcarbonyl or alkoxycarbonyl.

A particular embodiment of the present invention are compounds according to formula (I) as described herein, wherein $R^8$ is formyl.

A further particular embodiment of the present invention are compounds according to formula (I) as described herein, wherein $R^9$ is H or alkyl.

A more particular embodiment of the present invention are compounds according to formula (I) as described herein, wherein $R^9$ is alkyl.

Also a particular embodiment of the present invention are compounds according to formula (I) as described herein, wherein $R^9$ is methyl.

Particular examples of compounds of formula (I) as described herein are selected from
(3,4-dichlorophenyl)(1-methyl-1H-imidazol-5-yl)methanone;
(4-methoxyphenyl)(1-methyl-1H-imidazol-5-yl)methanone;
4-(1-ethyl-1H-imidazole-5-carbonyl)benzonitrile;
4-(1-isopropyl-1H-imidazole-5-carbonyl)benzonitrile;
3-fluoro-4-(1-methyl-1H-imidazole-5-carbonyl)benzonitrile;
(4-chloro-3-fluorophenyl)(1-methyl-1H-imidazol-5-yl)methanone;
3-fluoro-4-(1-isopropyl-1H-imidazole-5-carbonyl)benzonitrile;
(2,4-dichlorophenyl)(1-methyl-1H-imidazol-5-yl)methanone;
(3-chlorophenyl)(1-isopropyl-1H-imidazol-5-yl)methanone;
(3,4-dichlorophenyl)(1-isopropyl-1H-imidazol-5-yl)methanone;
(3,4-dichlorophenyl)(1-ethyl-1H-imidazol-5-yl)methanone;
4-(1-sec-butyl-1H-imidazole-5-carbonyl)benzonitrile;
(1-sec-butyl-1H-imidazol-5-yl)(4-chlorophenyl)methanone;
4-(1-cyclopropyl-1H-imidazole-5-carbonyl)benzonitrile;
(4-chlorophenyl)(1-cyclopropyl-1H-imidazol-5-yl)methanone;
4-(1-(2,2,2-trifluoro ethyl)-1H-imidazole-5-carbonyl)benzonitrile;
3-(1-methyl-1H-imidazole-5-carbonyl)benzonitrile;
(3-chlorophenyl)(1-methyl-1H-imidazol-5-yl)methanone;
(4-fluorophenyl)(1-methyl-1H-imidazol-5-yl)methanone;
(3-fluorophenyl)(1-methyl-1H-imidazol-5-yl)methanone;

1-methyl-6-(1-methyl-1H-imidazole-5-carbonyl)-3,4-dihydroquinolin-2(1H)-one;
6-(1-ethyl-1H-imidazole-5-carbonyl)-1-methyl-3,4-dihydroquinolin-2(1H)-one;
6-(1-isopropyl-1H-imidazole-5-carbonyl)-1-methyl-3,4-dihydroquinolin-2(1H)-one;
(1-sec-butyl-1H-imidazol-5-yl)(3-chlorophenyl)methanone;
(4-ethynylphenyl)(1-methyl-1H-imidazol-5-yl)methanone;
(4-tert-butylphenyl)(1-methyl-1H-imidazol-5-yl)methanone;
(3-chloro-4-fluorophenyl)(1-methyl-1H-imidazol-5-yl)methanone;
(3-chloro-4-fluorophenyl)(1-ethyl-1H-imidazol-5-yl)methanone;
(4-chloro-3-fluorophenyl)(1-ethyl-1H-imidazol-5-yl)methanone;
(4-tert-butylphenyl)(1-ethyl-1H-imidazol-5-yl)methanone;
3-(1-sec-butyl-1H-imidazole-5-carbonyl)benzonitrile;
(3-chloro-4-fluorophenyl)(1-isopropyl-1H-imidazol-5-yl)methanone;
(4-chloro-3-fluorophenyl)(1-isopropyl-1H-imidazol-5-yl)methanone;
(4-chloro-3-fluorophenyl)(1-cyclopropyl-1H-imidazol-5-yl)methanone;
(3-chloro-4-fluorophenyl)(1-cyclopropyl-1H-imidazol-5-yl)methanone;
2-chloro-4-(1-methyl-1H-imidazole-5-carbonyl)benzonitrile;
(1-methyl-1H-imidazol-5-yl)(4-(methylthio)phenyl)methanone;
benzo[b]thiophen-5-yl(1-methyl-1H-imidazol-5-yl)methanone;
2-fluoro-5-(1-methyl-1H-imidazole-5-carbonyl)benzonitrile;
2-chloro-4-(1-ethyl-1H-imidazole-5-carbonyl)benzonitrile;
(1-methyl-1H-imidazol-5-yl)(4-(methylsulfonyl)phenyl)methanone;
(1-ethyl-1H-imidazol-5-yl)(4-ethynylphenyl)methanone;
2-chloro-4-(1-isopropyl-1H-imidazole-5-carbonyl)benzonitrile;
(3-methoxy-4-(methylthio)phenyl)(1-methyl-1H-imidazol-5-yl)methanone;
(4-(ethylthio)phenyl)(1-methyl-1H-imidazol-5-yl)methanone;
(3-methoxy-4-(methylsulfonyl)phenyl)(1-methyl-1H-imidazol-5-yl)methanone;
(4-(ethylsulfonyl)phenyl)(1-methyl-1H-imidazol-5-yl)methanone;
(4-ethynylphenyl)(1-isopropyl-1H-imidazol-5-yl)methanone;
N-methyl-N-(4-(1-methyl-1H-imidazole-5-carbonyl)phenyl)acetamide;
3-(1-ethyl-1H-imidazole-5-carbonyl)benzonitrile;
3-(1-isopropyl-1H-imidazole-5-carbonyl)benzonitrile;
3-(1-cyclopropyl-1H-imidazole-5-carbonyl)benzonitrile;
N-(4-(1-isopropyl-1H-imidazole-5-carbonyl)phenyl)-N-methylacetamide;
(1-ethyl-1H-imidazol-5-yl)(3-methoxy-4-(methylthio)phenyl)methanone;
(1-isopropyl-1H-imidazol-5-yl)(3-methoxy-4-(methylthio)phenyl)methanone;
(1-cyclopropyl-1H-imidazol-5-yl)(3-methoxy-4-(methylthio)phenyl)methanone;
5-(1-ethyl-1H-imidazole-5-carbonyl)-2-fluorobenzonitrile;
2-fluoro-5-(1-isopropyl-1H-imidazole-5-carbonyl)benzonitrile;
5-(1-sec-butyl-1H-imidazole-5-carbonyl)-2-fluorobenzonitrile;
5-(1-cyclopropyl-1H-imidazole-5-carbonyl)-2-fluorobenzonitrile;
N-(4-(1-ethyl-1H-imidazole-5-carbonyl)phenyl)-N-methylacetamide;
(4-bromophenyl)(1-methyl-1H-imidazol-5-yl)methanone;
(1-ethyl-1H-imidazol-5-yl)(4-(ethylthio)phenyl)methanone;
(1-cyclopropyl-1H-imidazol-5-yl)(4-(ethylthio)phenyl)methanone;
(4-Ethylsulfanyl-phenyl)-(3-isopropyl-3#H!-imidazol-4-yl)-methanone;
(4-bromophenyl)(1-isopropyl-1H-imidazol-5-yl)methanone;
(1-methyl-1H-imidazol-5-yl)(4-(trifluoromethylthio)phenyl)methanone;
(1-ethyl-1H-imidazol-5-yl)(4-(trifluoromethylthio)phenyl)methanone;
(1-isopropyl-1H-imidazol-5-yl)(4-(trifluoromethylthio)phenyl)methanone;
(1-(pentan-3-yl)-1H-imidazol-5-yl)(4-(trifluoromethylthio)phenyl)methanone;
2-chloro-4-(5-(4-chlorobenzoyl)-1H-imidazol-1-yl)benzonitrile;
2-chloro-4-(5-(3,4-dichlorobenzoyl)-1H-imidazol-1-yl)benzonitrile;
(3-methoxy-4-(trifluoromethylthio)phenyl)(1-methyl-1H-imidazol-5-yl)methanone;
(1-ethyl-1H-imidazol-5-yl)(3-methoxy-4-(trifluoromethylthio)phenyl)methanone;
4-(1-(pentan-3-yl)-1H-imidazole-5-carbonyl)benzonitrile;
3-(1-(pentan-3-yl)-1H-imidazole-5-carbonyl)benzonitrile;
tert-butyl 4-(1-methyl-1H-imidazole-5-carbonyl)phenylcarbamate;
tert-butyl methyl(4-(1-methyl-1H-imidazole-5-carbonyl)phenyl)carbamate;
(1-methyl-1H-imidazol-5-yl)(4-(methylamino)phenyl)methanone;
N-methyl-N-(4-(1-methyl-1H-imidazole-5-carbonyl)phenyl)formamide;
tert-butyl 4-(1-ethyl-1H-imidazole-5-carbonyl)phenyl(methyl)carbamate;
N-(4-(1-ethyl-1H-imidazole-5-carbonyl)phenyl)-N-methylformamide;
(4-chlorophenyl)(1-(4-chlorophenyl)-1H-imidazol-5-yl)methanone;
(1-(4-chlorophenyl)-1H-imidazol-5-yl)(3,4-dichlorophenyl)methanone;
(4-chloro-3-fluorophenyl)(1-(4-chlorophenyl)-1H-imidazol-5-yl)methanone;
N-(4-(1-isopropyl-1H-imidazole-5-carbonyl)phenyl)-N-methylformamide;
4-(5-(4-chloro-3-fluorobenzoyl)-1H-imidazol-1-yl)benzonitrile;
4-(5-(4-chlorobenzoyl)-1H-imidazol-1-yl)benzonitrile;
4-(5-(3,4-dichlorobenzoyl)-1H-imidazol-1-yl)benzonitrile;

[3-(4-Chloro-phenyl)-3H-imidazol-4-yl]-(3,4-difluoro-phenyl)-methanone;
and pharmaceutically acceptable salts thereof.

Further particular examples of compounds of formula (I) as described herein are selected from
(3,4-dichlorophenyl)(1-methyl-1H-imidazol-5-yl)methanone;
4-(1-ethyl-1H-imidazole-5-carbonyl)benzonitrile;
1-methyl-6-(1-methyl-1H-imidazole-5-carbonyl)-3,4-dihydroquinolin-2 (1H)-one;
6-(1-ethyl-1H-imidazole-5-carbonyl)-1-methyl-3,4-dihydroquinolin-2 (1H)-one;
(1-methyl-1H-imidazol-5-yl)(4-(methylthio)phenyl)methanone;
2-chloro-4-(1-isopropyl-1H-imidazole-5-carbonyl)benzonitrile;
(3-methoxy-4-(trifluoromethylthio)phenyl)(1-methyl-1H-imidazol-5-yl)methanone;
4-(1-(pentan-3-yl)-1H-imidazole-5-carbonyl)benzonitrile;
N-(4-(1-ethyl-1H-imidazole-5-carbonyl)phenyl)-N-methylformamide;
4-(5-(4-chlorobenzoyl)-1H-imidazol-1-yl)benzonitrile;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text:
Ar=argon, DMF=N,N-dimethylformamide, DMSO=dimethyl sulfoxide, DCM=dichloromethane, EI=electron impact (ionization), ESI=electron spray ionization, HPLC=high performance liquid chromatography, h. V.=high vacuum, i. V.=in vacuo, mCPBA=m-chloroperbenzoic acid, NMR=nuclear magnetic resonance, MS=mass spectrum, rt=room temperature, TBTU=O-(benzotriazol-1-yl)-N,N,N',N'-tetramethyluronium tetrafluoroborate, THF=tetrahydrofuran, TMEDA=N,N,N',N'-tetramethylethylenediamine, TOSMIC=toluenesulfonylmethyl isocyanide.

The synthesis of compounds of the general formula (I) can be accomplished according to Scheme 1. Imidazoles 3, wherein $R^1$ is alkyl, haloalkyl, cycloalkyl, halocycloalkyl, cycloalkylalkyl, halocycloalkylalkyl, alkoxyalkyl, haloalkoxyalkyl or hydroxyalkyl, if not commercially available, can be synthesized by alkylation of free imidazole with the appropriate substituted or unsubstituted alkyl iodide or bromide and a base like $Cs_2CO_3$ in a polar solvent like acetonitrile at a temperature between RT and 80° C. (Scheme 1, step a). Iodination can then be achieved according to methods known by the man skilled in the art, by treatment with 2.4 equivalents of nBuLi, 2.4 equivalents of N,N,N',N'-tetramethylethylenediamine, and 1.4 equivalents of iodine in a mixture of THF and pentane to afford compound 4 (Scheme 1, step b). Transmetallation with, e.g., ethylmagnesium bromide or isopropylmagnesium chloride sets then the stage for the coupling with the appropriate benzaldehyde 5 which is preferably performed in dichloromethane at ambient temperature (Scheme 1, step c). Oxidation to the target molecules of formula (I) is most conveniently done by stirring over a large excess of $MnO_2$ (Schem 1, step d).

Scheme 1

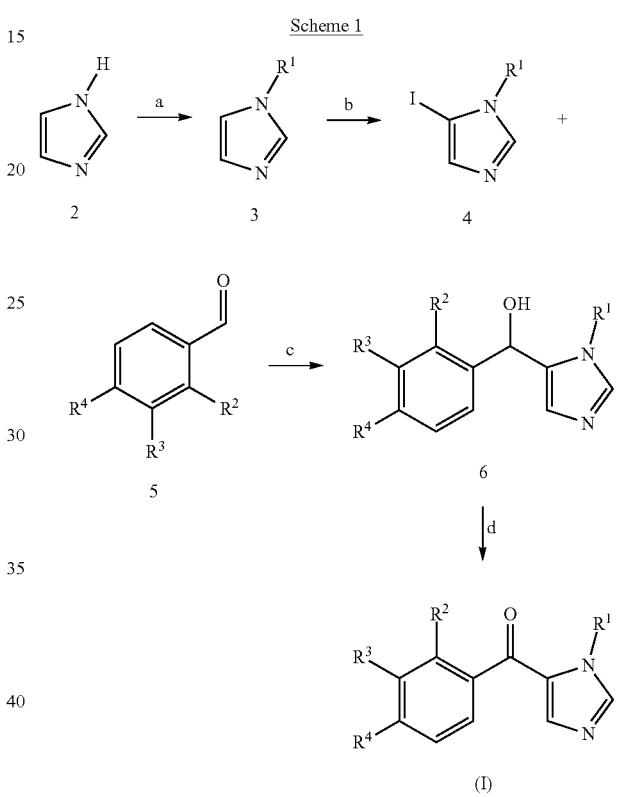

In a variation, the key intermediates 4a or 4b were obtained by electrophilic bromination of 3 with 1,3-dibromo-5,5-dimethylhydantoin or the respective diiodo-hydantoin in dichloromethane. (Scheme 2, a).

Scheme 2

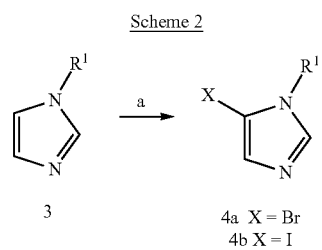

4a X = Br
4b X = I

Another variation starts with 5-bromo- or iodo-1H-imidazole which is alkylated with the appropriate alkyl halogenide or triflate, followed by separation of the two typically obtained regioisomers (Scheme 3, a).

Scheme 3

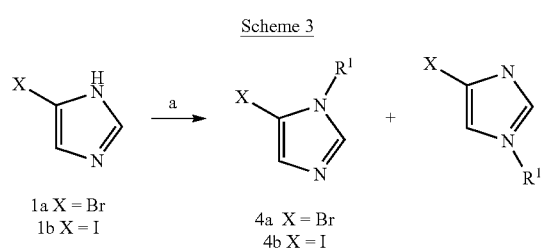

Yet another possibility to get access to compounds of formula (I) is illustrated in Scheme 4. 3-Alkyl-3H-imidazole-4-carboxylic acid 7, either commercially available or manufactured from the above prepared bromides or iodides with $CO_2$, is transformed according to standard procedures into the corresponding Weinreb amide 8 by treatment with, e.g., N,O-dimethylhydroxylamine hydrochloride, TBTU as condensing agent, and triethylamine in a mixture of THF and DMF (Scheme 4, step a). Ensuing reaction with the appropriate Grignard reagent 9a or the corresponding lithium-derivative 9b eventually delivers directly the desired compound of formula (I) (Scheme 4, step b).

Scheme 4

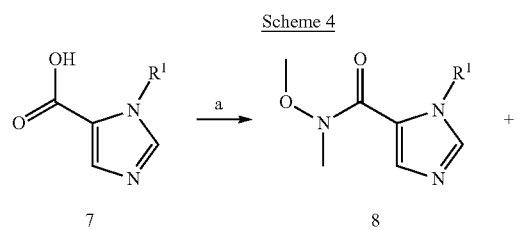

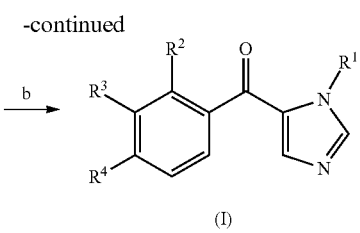

Compounds of the present invention in which $R^1$ is substituted aryl or substituted heteroaryl can be prepared according to Scheme 5. In brief, arylamines or heteroarylamines 10 are condensed with oxo-acetic acid ethyl ester 11 by heating in methanol under reflux yielding intermediates 12 which are further reacted with 1-isocyanomethanesulfonyl-4-methyl-benzene 13 in the presence of a base like $K_2CO_3$ in a polar solvent like methanol to provide key building blocks 3-aryl-3H-imidazole-4-carboxylic acid ethyl esters 14. These esters are then processed into Weinreb amides 15, either directly by treating them with O,N-dimethyl-hydroxylamine in the presence of dimethylaluminum chloride in a solvent like $CH_2Cl_2$, or indirectly by hydrolyzing them first to the corresponding carboxylic acids, e.g., by treatment with LiOH or NaOH in a mixture of methanol, THF, and water, followed by coupling those again with O,N-dimethyl-hydroxylamine in the presence of a condensing agent like TBTU and a base like triethylamine or Huenig's base in a mixture of DMF and tetrahydrofuran. Ensuing reaction with the appropriate Grignard-derivative 16 in tetrahydrofuran at ambient temperature provides the compounds of formula (I), wherein $R^1$ is substituted aryl or substituted heteroaryl.

Scheme 5

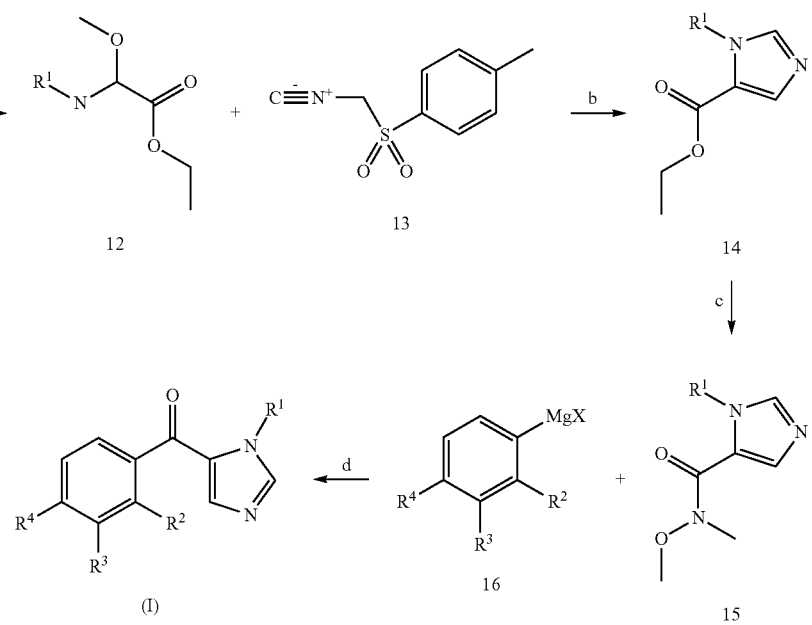

Also an embodiment of the present invention is a process to prepare a compound of formula (I) as defined above comprising the reaction of a compound of formula (II) in the presence of a compound of formula (III);

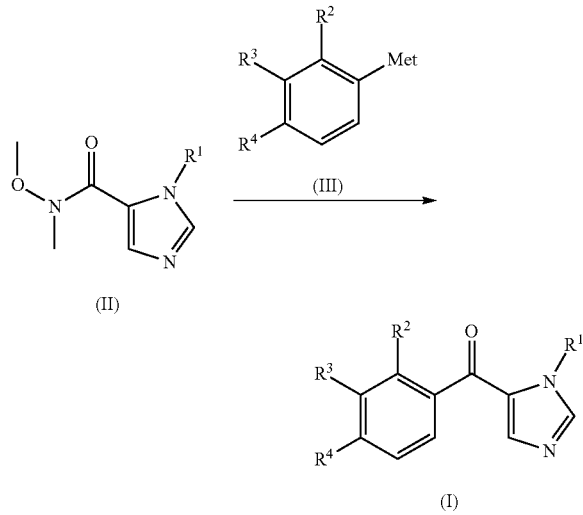

wherein R¹, R², R³ and R⁴ are as defined above and wherein Met is MgX or Li and X is halogen;

In particular, in a solvent such as THF, at a temperature comprised between −78° C. and RT, particularly between −10 and RT.

An object of the present invention is a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone for use as therapeutically active substance.

Also an object of the present invention is a compound according to formula (I) as described herein for use as therapeutically active substance.

Likewise an object of the present invention is a pharmaceutical composition comprising a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, and a therapeutically inert carrier.

Likewise an object of the present invention is a pharmaceutical composition comprising a compound according to formula (I) as described herein and a therapeutically inert carrier.

The present invention also relates to the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of chronic kidney disease.

The present invention also relates to the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of chronic kidney disease.

The present invention also relates to the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of congestive heart failure.

The present invention also relates to the use of a compound according to formula (I) as described herein for the treatment or prophylaxis of congestive heart failure.

The present invention also relates to the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of congestive heart failure.

The present invention also relates to the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of hypertension.

The present invention also relates to the use of a compound according to formula (I) as described herein for the treatment or prophylaxis of hypertension.

The present invention also relates to the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of primary aldosteronism.

The present invention also relates to the use of a compound according to formula (I) as described herein for the treatment or prophylaxis of primary aldosteronism.

The present invention also relates to the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of primary aldosteronism.

A particular embodiment of the present invention is a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of chronic kidney disease, congestive heart failure, hypertension, primary aldosteronism and Cushing syndrome.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of chronic kidney disease.

Also a particular embodiment of the present invention is a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of hypertension.

Also a particular embodiment of the present invention is a compound according to formula (I) as described herein for the treatment or prophylaxis of hypertension.

Also a particular embodiment of the present invention is a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the preparation of a medicament for the treatment or prophylaxis of chronic kidney disease, congestive heart failure, hypertension, primary aldosteronism and Cushing syndrome.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

Also an embodiment of the present invention is the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the preparation of a medicament for the treatment or prophylaxis of chronic kidney disease.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the preparation of a medicament for the treatment or prophylaxis of congestive heart failure.

Also an embodiment of the present invention is the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the preparation of a medicament for the treatment or prophylaxis of congestive heart failure.

Also an embodiment of the present invention is the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the preparation of a medicament for the treatment or prophylaxis of hypertension.

Also an embodiment of the present invention is the use of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone, for the preparation of a medicament for the treatment or prophylaxis of primary aldosteronism.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein or selected from (4-chlorophenyl)[1-(1-methylethyl)-1H-imidazol-5-yl]-methanone, (1-butyl-1H-imidazol-5-yl)(4-chlorophenyl)-methanone, [4-(1-methylethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, (3-bromophenyl)(1-methyl-1H-imidazol-5-yl)-methanone.

Also an embodiment of the present invention is a method for the treatment or prophylaxis of primary aldosteronism, which method comprises administering an effective amount of a compound according to formula (I) as described herein.

Also an embodiment of the present invention are compounds of formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynomolgus CYP11B1 or cynomolgus CYP11B2 enzyme activity. Importantly, the identified cell line G-402 expresses co-factors (adrenodoxin and adrenodoxin reductase) important for the activity of the CYP11 family, and no relevant enzyme activity of the CYP11 family (in comparison to H295R cells) was detected in these cells. Therefore the G-402 cell line is uniquely suited as a host cell for the ectopic expression of enzymes from the CYP11 family.

G-402 cells can be obtained from ATCC(CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B1) as a substrate.

G-402 cells expressing CYP11 constructs were established as described above and maintained in McCoy's 5a Medium Modified, ATCC Catalog No. 30-2007 containing 10% FCS and 400 µg/ml G418 (Geneticin) at 37° C. under an atmosphere of 5% CO2/95% air. Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 µM Deoxycorticosterone and variable amounts of inhibitors; Cyp11B1 enzyme activity was tested in presence of 1 µM Deoxycortisol and variable amounts of inhibitors.

| Example | EC50 human CYP11B1 µM | EC50 human CYP11B2 µM |
|---|---|---|
| 1 | 0.1954 | 0.0623 |
| 2 | 0.3684 | 0.0116 |
| 3 | 0.1674 | 0.0049 |
| 4 | 3.5002 | 0.1178 |
| 5 | 0.0468 | 0.0026 |
| 6 | 0.0045 | 0.0008 |
| 7 | 0.0659 | 0.0044 |
| 8 | 2.4972 | 0.0986 |
| 9 | 0.187 | 0.0077 |
| 10 | 0.0703 | 0.0108 |
| 11 | 1.8009 | 0.2157 |
| 12 | 0.0053 | 0.0013 |
| 13 | 0.0056 | 0.0021 |
| 14 | 0.0018 | 0.0005 |
| 15 | 0.02 | 0.0018 |
| 16 | 0.001 | 0.0007 |
| 17 | 0.0035 | 0.0003 |
| 18 | 0.0287 | 0.0023 |
| 19 | 0.0529 | 0.0061 |
| 20 | 0.1904 | 0.0235 |
| 21 | 8.7124 | 0.5827 |
| 22 | 0.543 | 0.0326 |
| 23 | 0.1509 | 0.0493 |
| 24 | 0.6726 | 0.0652 |
| 25 | 7.8811 | 0.077 |
| 26 | 1.1171 | 0.0197 |
| 27 | 0.1527 | 0.0069 |
| 28 | 0.0227 | 0.0141 |
| 29 | 0.259 | 0.0203 |
| 30 | 9.8786 | |
| 31 | 7.8354 | 0.1967 |
| 32 | 0.3036 | 0.0117 |
| 33 | 0.0317 | 0.0037 |
| 34 | 0.033 | 0.0027 |
| 35 | 1.6856 | 3.6691 |
| 36 | 1.7517 | 0.0587 |
| 37 | 0.0782 | 0.0063 |
| 38 | 0.0039 | 0.0039 |
| 39 | 0.0033 | 0.0007 |
| 40 | 0.0148 | 0.0023 |
| 41 | 0.021 | 0.0035 |
| 42 | 0.0893 | 0.0074 |
| 43 | 1.5325 | 0.0284 |
| 44 | 1.0746 | 0.0409 |
| 45 | 11.2508 | 0.5754 |
| 46 | 0.0254 | 0.0023 |
| 47 | | 3.5332 |
| 48 | 0.033 | 0.0043 |
| 49 | 0.001 | 0.0002 |
| 50 | 0.6867 | 0.0148 |
| 51 | 3.2482 | 0.102 |
| 54 | 0.0068 | 0.0005 |
| 55 | | 0.923 |
| 56 | 1.208 | 0.1087 |
| 57 | 0.2026 | 0.026 |
| 58 | 0.8897 | 0.0872 |
| 59 | 5.044 | 0.0513 |
| 60 | 0.0843 | 0.004 |
| 61 | 0.0087 | 0.0002 |
| 62 | 0.0461 | 0.0028 |
| 63 | 3.438 | 0.335 |
| 64 | 0.4484 | 0.323 |
| 65 | 0.0882 | 0.0215 |
| 66 | 2.2131 | 0.4472 |
| 67 | 9.9138 | 0.2914 |
| 68 | 0.4876 | 0.0186 |
| 69 | 0.3292 | 0.0844 |
| 70 | 0.3639 | 0.0228 |
| 71 | 0.2526 | 0.0053 |
| 72 | 0.0101 | 0.0052 |
| 73 | | 0.3902 |
| 74 | 1.3248 | 0.2354 |
| 75 | 0.7595 | 0.0899 |
| 76 | 0.2642 | 0.0427 |
| 77 | 0.0098 | 0.0019 |
| 78 | 0.1449 | 0.0037 |
| 79 | 1.5764 | 0.0148 |
| 80 | 0.6338 | 0.0129 |
| 81 | 0.199 | 0.0159 |

-continued

| Example | EC50 human CYP11B1 μM | EC50 human CYP11B2 μM |
|---|---|---|
| 82 | 0.0033 | 0.0002 |
| 83 | 0.057 | 0.0057 |
| 85 | 12.549 | |
| 86 | 3.7466 | 1.6247 |
| 87 | 30.3613 | 0.1863 |
| 88 | 1.2855 | 2.2019 |
| 89 | 0.7436 | 0.0294 |
| 90 | 3.6212 | 0.0026 |
| 91 | 0.4392 | 0.0042 |
| 92 | 0.1321 | 0.0032 |
| 93 | 0.3488 | 0.0117 |
| 94 | 0.0846 | 0.0144 |
| 95 | 0.0718 | 0.0022 |
| 96 | 0.199 | 0.0056 |
| 97 | 0.0746 | 0.0034 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 50 uM, more particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein display also variable inhibition of CYP11B1. These compounds may be used for the inhibition of CYP11B1 in combination with variable inhibition of CYP11B2. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), renal conditions, liver conditions, vascular conditions, inflammatory conditions, pain, retinopathy, neuropathy (such as peripheral neuropathy), insulinopathy, edema, endothelial dysfunction, baroreceptor dysfunction; fibrotic diseases, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, heart failure, hypertrophic cardiomyopathy, impaired arterial compliance, impaired diastolic filling, ischemia, left ventricular hypertrophy, myocardial and vascular fibrosis, myocardial infarction, myocardial necrotic lesions, myocardial necrotic lesions cardiac arrhythmias, prevention of sudden cardiac death, restenosis, stroke, vascular damage.

Renal conditions include acute and chronic renal failure, end-stage renal disease, decreased creatinine clearance, decreased glomerular filtration rate, diabetic nephropathy, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, nephropathy, proteinuria, reduced renal blood flow, renal arteriopathy, swelling and proliferation of intracapillary (endothelial and mesangial) and/or extracapillary cells (crescents)).

Liver conditions include, but are not limited to, liver cirrhosis, liver ascites, hepatic congestion, nonalcoholic steatohepatitis and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, splenic congestion, liver ascites, respiratory or lung congestion, and the like.

Insulinopathies include, but are not limited to, insulin resistance, Type I diabetes mellitus, Type II diabetes mellitus, glucose sensitivity, pre-diabetic state, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In another embodiment, the cardiovascular condition is heart failure.

In another embodiment, the cardiovascular condition is left ventricular hypertrophy.

In another embodiment, the cardiovascular condition is stroke.

In another embodiment, the compounds of formula (I) or their pharmaceutically acceptable salts and esters can be used for the treatment or prophylaxis of renal condition.

In another embodiment, the renal condition is nephropathy.

In another embodiment, the compounds of formula (I) or their pharmaceutically acceptable salts and esters can be used for the treatment or prophylaxis of Type II diabetes mellitus.

In another embodiment, the compounds of formula (I) or their pharmaceutically acceptable salts and esters can be used for the treatment or prophylaxis of Type I diabetes mellitus.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

All examples and intermediates were prepared under argon atmosphere if not specified otherwise.

Intermediate 1a

1-Ethyl-5-iodo-1H-imidazole

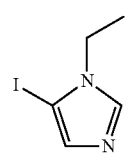

In a 100 mL three-necked flask, TMEDA (2.86 g, 3.72 ml, 24.7 mmol, Eq: 2.37) was combined with pentane (10 ml) to give a colorless solution. N-BuLi 1.6M in hexane (15.6 ml, 25.0 mmol, Eq: 2.4), followed by 1-ethyl-1H-imidazole (1 g, 10.4 mmol, Eq: 1.00) were added dropwise at −25° C. for 30 min. The reaction mixture was stirred at RT for 1 h (light yellow suspension). Afterwards, the suspension was cooled to −65° C. and THF anhydrous (30 ml) was added (−65° C. to −48° C.). A solution of iodine (3.83 g, 15.1 mmol, Eq: 1.45) in THF anhydrous (20 ml) was added dropwise to the reaction mixture (internal temperature remained below −55° C.)=>brown suspension. Stirring was continued as the reaction was gradually warmed to 0° C. during 1.3 hours (brown milky solution). Eventually, the reaction was quenched by adding 4 mL of methanol. Work up: The reaction mixture was poured into 50 mL sat. Na2SO3 and extracted with EtOAc (2×100 mL). The organic layers were combined, washed with brine, dried over $Na_2SO_4$, and concentrated i. V. Purification: The crude material was purified by flash chromatography (silica gel, 50 g, 20% to 100% EtOAc in heptane) to provide in the more polar fractions 417 mg of the desired title compound as yellow oil. MS (ESI): 222.9 $[M+H]^+$.

Intermediate 1a'

5-Bromo-1-ethyl-1H-imidazole

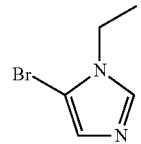

In a 750 mL three-necked flask, 1-ethyl-1H-imidazole (3 g, 3.13 ml, 31.2 mmol, Eq: 1.00) was combined with DCM (140 ml) to give a colorless solution. 1,3-Dibromo-5,5-dimethylimidazolidine-2,4-dione (4.55 g, 15.9 mmol, Eq: 0.51), dissolved in DCM (140 ml), was added dropwise at 0° C. during 20 min. to give a dark green solution. The reaction mixture was stirred at 0° C. for another 2 h. Work up: The reaction mixture was poured into 125 mL sat $Na_2SO_3$, extracted with DCM (2×100 mL) and washed with H2O/brine (20 ml). The organic layers were combined, washed with brine, dried over $Na_2SO_4$, and concentrated i. V. Purification: The crude product was purified by flash chromatography (silica gel, 400 g, 5% MeOH in DCM) go give 1.66 g of pure title compound as yellow liquid. MS (ESI): 175.0, 177.0 $[M+H]^+$.

Intermediate 1b

5-Iodo-1-isopropyl-1H-imidazole

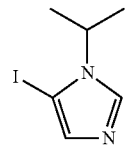

In a 200 mL three-necked flask, TMEDA (2.42 g, 3.14 ml, 20.8 mmol, Eq: 2.37) was combined with pentane (25 ml) to give a colorless solution. N-BuLi 1.6M in hexane (13.2 ml, 21.1 mmol, Eq: 2.4) and then 1-isopropyl-1H-imidazole (1.29 g, 8.78 mmol, Eq: 1.00) were added dropwise at −25° C. The reaction mixture was stirred for 1 hour at RT (yellow/light brown suspension). Afterwards, the suspension was cooled down to −65° C. and THF (15 ml) was added (−66° C. to −54° C.). A solution of iodine (3.23 g, 12.7 mmol, Eq: 1.45) in THF (30 ml) was added dropwise to the reaction mixture (internal temperature remained below −55° C., brown suspension). The reaction was warmed to 0° C. during 1 hour and stirred at that temperature for another 30 min. Work up: 10 mL MeOH were added at 0° C., followed by 15 mL brine. Extraction was done with sat. Na2SO3 sol. (100 ml) and EtOAc (3×100 ml). The organic layers were washed with brine, combined, dried over Na$_2$SO$_4$, and concentrated i. V. Purification: The crude material was purified by flash chromatography (silica gel, 70 g, 50% to 100% EtOAc in heptane) to provide in the more polar fractions 322 mg of the desired title compound as yellow solid. MS (ESI): 236.9 [M+H]$^+$.

Intermediate 1b'

5-Bromo-1-isopropyl-1H-imidazole

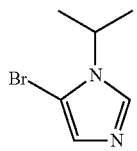

In a 250 mL round-bottomed flask, 1-isopropyl-1H-imidazole (1.635 g, 14.8 mmol, Eq: 1.00) was combined with DCM (70 ml) to give a colorless solution. 1,3-Dibromo-5,5-dimethylimidazolidine-2,4-dione (2.16 g, 7.57 mmol, Eq: 0.51), dissolved in DCM (70 ml), was added dropwise at 0° C. during 20 min. to give a orange solution; stirring was continued at 0° C. for 2 h. Work up: the reaction mixture was poured into 125 mL sat Na$_2$SO$_3$, extracted with DCM (2×100 mL), the combined organic layers were washed with H$_2$O/brine (20 ml), dried over Na$_2$SO$_4$ and concentrated i. V. Twofold purification by flash chromatography (silica gel, 80 g, 1% to 10% MeOH in DCM and silica gel; 80 g, 5% MeOH in DCM) produced finally 628 mg of the title product as light brown oil. MS (ESI): 189.1, 191.2 [M+H]$^+$.

Intermediate 1c

1-Cyclopropyl-5-iodo-1H-imidazole

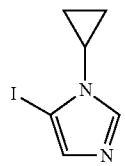

In a 50 mL three-necked flask, 1-cyclopropyl-1H-imidazole (200 mg, 1.85 mmol, Eq: 1.00) was combined with DCM (18 ml) to give a colorless solution. 1,3-Diiodo-5,5-dimethylimidazolidine-2,4-dione (358 mg, 943 μmol, Eq: 0.51) was added at 5° C. (orange solution), followed by methanesulfonic acid (355 mg, 240 μl, 3.7 mmol, Eq: 2), and the reaction mixture was allowed to proceed over night at rt. Work up: The reaction mixture was quenched with sat NaHCO$_3$ 10 mL and extracted with DCM (2×25 mL). The organic layers were washed with sat. Na$_2$SO$_3$ sol., then with H$_2$O/NaCl sol. The organic layers were combined, dried over Na$_2$SO$_4$ and concentrated i. V. The crude material was carefully purified by flash chromatography (silica gel, 20 g, 30% to 100% EtOAc in heptane) to provide 36 mg of the title compound as colorless oil. MS (ESI): 234.8 [M+H]$^+$.

Intermediate 1c'

5-Bromo-1-cyclopropyl-1H-imidazole

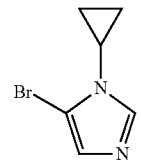

In a 350 mL four-necked flask, 1-cyclopropyl-1H-imidazole (2.58 g, 23.9 mmol, Eq: 1.00) was combined with DCM (100 ml) to give a colorless solution. 1,3-Dibromo-5,5-dimethylimidazolidine-2,4-dione (3.48 g, 12.2 mmol, Eq: 0.51), dissolved in dichloromethane (100 ml) was added dropwise at 5° C. and the reaction mixture stirred at 5° C. for 2.5 hr. Work up: The reaction mixture was quenched with 100 ml Na$_2$SO$_3$ sol. and extracted with DCM (2×200 ml). The organic layers were washed with H$_2$O/NaCl sol, dried over Na$_2$SO$_4$ and concentrated i. V. The crude product was purified by flash chromatography (silica gel, 120 g, 25% to 100% EtOAc in heptane) to give 1.21 g of the title compound as colorless oil. MS (ESI): 187.9/189.1 [M+H]$^+$.

Intermediate 1d 1-sec-Butyl-5-iodo-1H-imidazole

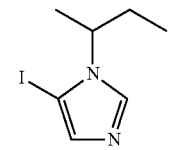

In a 100 mL three-necked flask, TMEDA (3.17 g, 4.12 ml, 27.3 mmol, Eq: 2.37) was combined with pentane (10 ml) to give a colorless solution. nBuLi 1.6M in hexane (17.3 ml, 27.6 mmol, Eq: 2.4), followed by 1-sec-butyl-1H-imidazole (1.43 g, 11.5 mmol, Eq: 1.00), were added dropwise at −25° C. for 30 min. The reaction mixture was stirred at RT for 1 h to give a light yellow suspension. It was then cooled to −65° C., anhydrous THF (30 ml) was added (−65° C. to −42° C.), and finally dropwise a solution of iodine (4.24 g, 16.7 mmol, Eq: 1.45) in anhydrous THF (20 ml) to keep the internal temperature below −55° C.=>brown suspension. Stirring was continued as the reaction was gradually warmed to 0° C. over 1.5 hours (brown milky solution), before the reaction was quenched by adding 4 mL of methanol. Work up: The reaction mixture was poured into 50 mL sat. Na$_2$SO$_3$ and extracted with EtOAc (2×100 mL). The organic layers were combined, washed with brine, dried over Na$_2$SO$_4$, and the solvents removed i. V. Purification: The crude material was purified by flash chromatography (silica gel, 70 g, 20% to 100% EtOAc in heptane) to afford in the more polar fractions 794 mg of the desired title compound as light yellow solid. MS (ESI): 250.9 [M+H]$^+$.

Intermediate 1d'

5-Bromo-1-sec-butyl-1H-imidazole

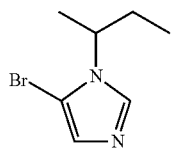

In a 150 mL round-bottomed flask, 1-sec-butyl-1H-imidazole (0.94 g, 7.57 mmol, Eq: 1.00) was combined with DCM (50 ml) to give a colorless solution. 1,3-Dibromo-5,5-dimethylimidazolidine-2,4-dione (1.1 g, 3.86 mmol, Eq: 0.51) in DCM (50 ml) was added dropwise at 0° C. during 20 min. to give a orange solution, and the mixture was stirred at 0° C. for additional 2 h. Work up: The reaction mixture was poured into 125 mL sat. Na$_2$SO$_3$ sol., extracted with DCM (2×100 mL) and washed with H$_2$O/brine (50 ml). The combined organic layers were dried over Na$_2$SO$_4$ and concentrated i. V. Purification: The crude material was purified by flash chromatography (silica gel, 120 g, 20% to 50% EtOAc in heptane) to yield 374 mg of the title product as white solid. MS (ESI): 203.0, 205.1 [M+H]$^+$.

Intermediate 1e

5-Iodo-1-(2,2,2-trifluoro ethyl)-1H-imidazole

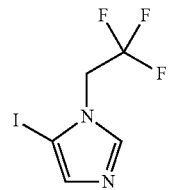

In a 50 mL three-necked flask, 4-iodo-1H-imidazole (0.500 g, 2.58 mmol, Eq: 1.00) was combined under Ar with THF (7 ml) to give a colorless solution. Sodium hydride 55% (337 mg, 7.73 mmol, Eq: 3) was added at 0° C. (exothermic reaction, temperature rose to 17° C.). The reaction mixture was stirred at RT for 30 min. and then cooled down again to 0° C., before 2,2,2-trifluoroethyl trifluoromethanesulfonate (1.2 g, 5.16 mmol, Eq: 2), dissolved in THF (3 ml), was added. The white suspension was stirred at RT for additional 1.5 hours when TLC indicated that the reaction was complete. Work up: The reaction mixture was poured into 10 mL H$_2$O and extracted with EtOAc (2×15 mL). The organic layers were combined, washed with brine, dried over Na$_2$SO$_4$, and concentrated i. V. Purification: The crude product was purified by flash chromatography (silica gel, 70 g, 0% to 60% EtOAc in heptane) to yield 80 mg of the desired title compound as off-white solid, besides 619 mg of the unwanted 4-iodo-1-(2,2,2-trifluoro-ethyl)-1H-imidazole. MS (ESI): 276.9 [M+H]$^+$.

Intermediate 1f'

5-Bromo-1-(1-ethyl-propyl)-1H-imidazole

Was prepared in analogy to intermediate 1d', but using 1-(1-ethyl-propyl)-1H-imidazole as starting material instead of 1-sec-butyl-1H-imidazole, as light yellow oil. MS (ESI): 217.1, 219.2 [M+H]$^+$.

Intermediate 2a

1-Methyl-2-oxo-1,2,3,4-tetrahydro-quinoline-6-carbaldehyde

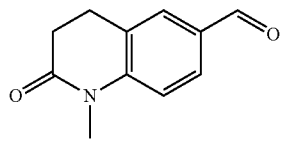

In a 10 mL three-necked flask, 2-oxo-1,2,3,4-tetrahydro-quinoline-6-carbaldehyde (0.250 g, 1.43 mmol, Eq: 1.00) was combined with acetonitrile (5 ml) to give a yellow suspension. DMF (3 ml) was added, followed by cesium carbonate (511 mg, 1.57 mmol, Eq: 1.1), and the reaction mixture was stirred at RT for 15 min. Iodomethane (223 mg, 98.6 µl, 1.57 mmol, Eq: 1.1) was added and stirring was continued at RT overnight. Work up: the reaction mixture was poured into 10 mL H$_2$O and extracted with EtOAc (2×15 mL). The organic layers were combined, washed with brine, dried over Na$_2$SO$_4$, and concentrated i. V. Purification: The crude product was purified by flash chromatography (silica gel, 20 g, 30% to 70% EtOAc in heptane) to afford 227 mg of the title compound as white solid. MS (ESI): 190.3 [M+H]$^+$.

Intermediate 2b

2-Chloro-4-formylbenzonitrile

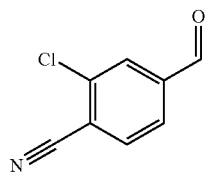 [SMILES: N#Cc1ccc(C=O)cc1Cl]

In a 25 mL three-necked flask, isopropylmagnesium chloride 2M in THF (751 µl, 1.5 mmol, Eq: 1.3) was combined with THF (10 ml) under Ar to give a colorless solution. The reaction mixture was cooled down to 0° C. and 4-bromo-2-chlorobenzonitrile (0.250 g, 1.15 mmol, Eq: 1.00), dissolved in THF (2.5 ml), was added dropwise during 10 min keeping the temperature below 2° C. (yellow solution). The metallation was allowed to proceed at 0° C. for additional 2 hours. A solution of N-formylpiperidine (170 mg, 167 µl, 1.5 mmol, Eq: 1.3) in THF (2.5 ml) was added, and the reaction was stirred at 0° C. for 2 hours (yellow solution). Work up: The reaction mixture was poured into 10 mL 1 M HCl and extracted with EtOAc (1×20 mL). The organic layers were combined, washed with water, dried over $Na_2SO_4$, and concentrated i. V. Purification: The crude material was purified by flash chromatography (silica gel, 20 g, 0% to 50% EtOAc in heptane) to yield 82 mg of the desired title product as white solid. MS (GC-EI): 165 $[M]^+$.

Example 1

Step 1

(4-Chloro-phenyl)-(3-methyl-3H-imidazol-4-yl)-methanol

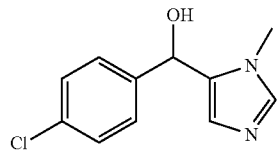

In a 10 mL two-necked flask, 5-iodo-1-methyl-1H-imidazole (150 mg, 721 µmol, Eq: 1.00) was combined with DCM (3 ml) to give a colorless solution. Ethylmagnesium bromide (264 µl, 793 µmol, Eq: 1.1) was added at rt over 2 min (white precipitate). After stirring for 1 hr, the reaction mixture was cooled to 0° C., and a solution of 4-chlorobenzaldehyde (132 mg, 937 µmol, Eq: 1.3) in DCM (2 ml) was added dropwise, and the mixture was stirred at rt. TLC after 2 h indicated the absence of starting material. Work up: The reaction mixture was quenched with sat. $NaHCO_3$ (10 mL) and extracted with AcOEt (2×20 mL). The organic layers were washed with $H_2O$/NaCl sol., the organic layers were combined, dried over $Na_2SO_4$, and concentrated i. V. The product was precipitated from DCM, filtered and dried on h. V. MS (ESI): 223.1/225.0 $[M+H]^+$.

The reaction can equally well be performed in THF or a mixture of THF and DCM.

Step 2

(4-Chloro-phenyl)-(3-methyl-3H-imidazol-4-yl)-methanone

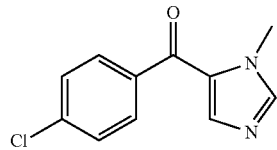

In a 25 mL round-bottomed flask, the above prepared (4-chlorophenyl)(1-methyl-1H-imidazol-5-yl)methanol (106 mg, 476 µmol, Eq: 1.00) was combined with DCM (6 ml) to give a white suspension. THF (15 ml) was added to dissolve all starting material. Manganese dioxide (828 mg, 9.52 mmol, Eq: 20) was added and the reaction mixture was vigorously stirred for 4 hr at rt. Work up: The reaction mixture was filtered through celite and washed with DCM. The crude material was purified by flash chromatography (silica gel, 10 g, 5% MeOH in DCM) to yield 68 mg of the title compound as white semisolid. MS (ESI): 221.1/223.1 $[M+H]^+$.

Example 2

4-(3-Methyl-3H-imidazole-4-carbonyl)-benzonitrile

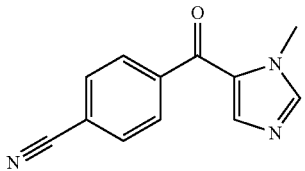 [SMILES: Cn1cncc1C(=O)c1ccc(C#N)cc1]

was synthesized in analogy to example 1, but using in step 1 4-formyl-benzonitrile instead of 4-chlorobenzaldehyde, as white foam. MS (ESI): 214.1 $[M+H]^+$.

Example 3

Step 1

3-Methyl-3H-imidazole-4-carboxylic acid methoxy-methyl-amide

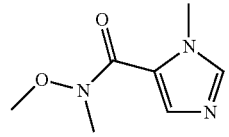

In a 100 mL two-necked flask, 1-methyl-1H-imidazole-5-carboxylic acid (1 g, 7.93 mmol, Eq: 1.00) was combined with THF (30 ml) and DMF (15 ml) to give a brown suspension. TBTU (3.56 g, 11.1 mmol, Eq: 1.4) and $Et_3N$ (2.41 g, 3.32 ml, 23.8 mmol, Eq: 3) were added at rt and the solution was stirred for 20 min. N,O-dimethylhydroxylamine hydrochloride (928 mg, 9.52 mmol, Eq: 1.2) was added at rt and the reaction mixture was stirred for 18 hr at rt. Work up: The crude reaction mixture was concentrated i. V. to remove THF and then on h. V. to remove the major part of DMF. The residue was poured into 10 mL sat $NH_4Cl$+30 ml $H_2O$ and extracted with DCM (3×75 mL) and then EtOAc/THF (75 ml). The organic layers were washed with brine, dried over $Na_2SO_4$, and concentrated i. V. The crude material was purified by flash chromatography (2× Amine-Si, 50 g, 50% to 100% EtOAc in heptane) to give 1.18 g of the title compound as light yellow oil. MS (ESI): 170.1 $[M+H]^+$.

Step 2

(3,4-Dichloro-phenyl)-(3-methyl-3H-imidazol-4-yl)-methanone

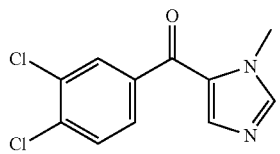 [SMILES: Cn1cncc1C(=O)c1ccc(Cl)c(Cl)c1]

In a 10 mL two-necked flask, the above prepared N-methoxy-N,1-dimethyl-1H-imidazole-5-carboxamide (100 mg, 591 µmol, Eq: 1.00) was combined with THF (3.00 ml) to give a light yellow solution. The reaction mixture was cooled to 0° C. and (3,4-dichlorophenyl)magnesium bromide (4.14 ml, 2.07 mmol, Eq: 3.5) was slowly added while keeping the temperature below 2° C. The mixture was stirred for 1 h at 0° C. and for 2 h at RT when MS and TLC showed the absence of starting material. The reaction mixture was quenched with ice water and extracted with 3×10 mL of AcOEt. The organic layers were washed with brine, dried over Na$_2$SO$_4$, and concentrated i. V. The crude material was purified by flash chromatography (silica gel, 10 g, 5% MeOH in DCM) to yield, after trituration with AcOEt, 89 mg of the title compound as white powder. MS (ESI): 254.9, 257.0, 259.1 [M+H]$^+$.

Example 4

(4-Methoxy-phenyl)-(3-methyl-3H-imidazol-4-yl)-methanone

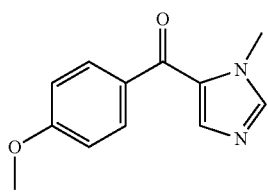 [SMILES: COc1ccc(C(=O)c2cncn2C)cc1]

In a 25 mL three-necked flask, 1-bromo-4-methoxybenzene (174 mg, 116 µl, 931 µmol, Eq: 1.5) was combined with THF (10 ml) to give a colorless solution. The solution was cooled to −75° C. At this temperature, nBuLi (582 µl, 931 µmol, Eq: 1.5) was added during 10 min and the reaction mixture was stirred for 30 min at −75° C., before a solution of the above prepared N-methoxy-N,1-dimethyl-1H-imidazole-5-carboxamide (105 mg, 621 µmol, Eq: 1.00) in THF (5 ml) was added during 10 min. The reaction was then allowed to proceed for 4 h at ambient temperature. Work up: The reaction mixture was quenched with sat. NaHCO$_3$ 10 mL and extracted with EtOAc (2×25 mL). The organic layers were washed with H$_2$O/NaCl sol., the organic layers were combined, dried over Na$_2$SO$_4$, and concentrated i. V. The crude material was purified by flash chromatography (silica gel, 50 g, 2% to 10% MeOH in DCM) to provide, after trituration with AcOEt/heptane, 23 mg of the title product as light yellow powder. MS (ESI): 217.3 [M+H]$^+$.

Example 5

4-(3-Ethyl-3H-imidazole-4-carbonyl)-benzonitrile

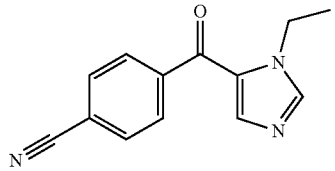 [SMILES: CCn1cncc1C(=O)c1ccc(C#N)cc1]

was prepared in analogy to example 2, but starting the sequence with 1-ethyl-5-iodo-1H-imidazole (intermediate 1a) as white solid. MS (ESI): 226.1 [M+H]$^+$.

Example 6

4-(3-Isopropyl-3H-imidazole-4-carbonyl)-benzonitrile

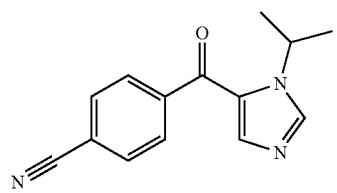 [SMILES: CC(C)n1cncc1C(=O)c1ccc(C#N)cc1]

was prepared in analogy to example 2, but starting the sequence with 5-iodo-1-isopropyl-1H-imidazole (intermediate 1b) as white semisolid. MS (ESI): 242.3 [M+H]$^+$.

Example 7

(4-Chloro-phenyl)-(3-ethyl-3H-imidazol-4-yl)-methanone

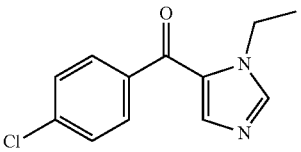 [SMILES: CCn1cncc1C(=O)c1ccc(Cl)cc1]

was prepared in analogy to example 1, but starting the sequence with 1-ethyl-5-iodo-1H-imidazole (intermediate 1a) as light yellow oil. MS (ESI): 235.0/237.0 [M+H]$^+$.

Example 8

3-Fluoro-4-(3-methyl-3H-imidazole-4-carbonyl)-benzonitrile

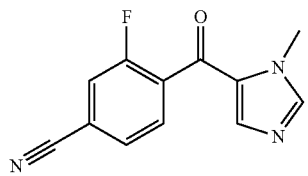 [SMILES: Cn1cncc1C(=O)c1ccc(C#N)cc1F]

was synthesized in analogy to example 1, but using in step 1 3-fluoro-4-formylbenzonitrile instead of 4-chlorobenzaldehyde, as white solid. MS (ESI): 230.1 [M+H]$^+$.

Example 9

(4-Chloro-3-fluoro-phenyl)-(3-methyl-3H-imidazol-4-yl)-methanone

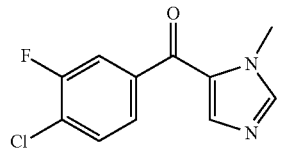 [SMILES: Cn1cncc1C(=O)c1ccc(Cl)c(F)c1]

was synthesized in analogy to example 3, but using in step 2 (4-chloro-3-fluorophenyl)magnesium bromide (THF) instead of (3,4-dichlorophenyl)magnesium bromide, as white powder. MS (ESI): 238.9 [M+H]$^+$.

Example 10

3-Fluoro-4-(3-isopropyl-3H-imidazole-4-carbonyl)-benzonitrile

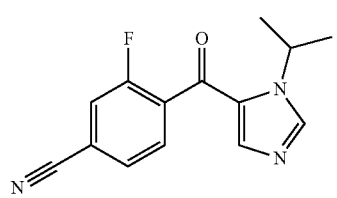 [SMILES: CC(C)n1cncc1C(=O)c1ccc(C#N)cc1F]

was synthesized in analogy to example 6, but using in step 1 3-fluoro-4-formyl-benzonitrile instead of 4-chlorobenzaldehyde, as white semisolid. MS (ESI): 258.0 [M+H]$^+$.

Example 11

(2,4-Dichloro-phenyl)-(3-methyl-3H-imidazol-4-yl)-methanone

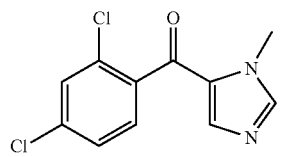 [SMILES: Cn1cncc1C(=O)c1ccc(Cl)cc1Cl]

was prepared in analogy to example 1, but using in step 1 2,4-dichloro-benzaldehyde instead of 4-chlorobenzaldehyde, as light-yellow solid. MS (ESI): 255.0, 257.0, 259.0 [M+H]$^+$.

Example 12

(3-Chloro-phenyl)-(3-isopropyl-3H-imidazol-4-yl)-methanone

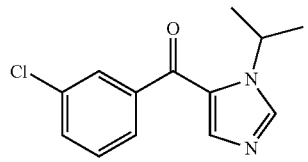 [SMILES: CC(C)n1cncc1C(=O)c1cccc(Cl)c1]

was synthesized in analogy to example 6, but using in step 1 3-chloro-benzaldehyde instead of 4-formyl-benzonitrile, as colorless oil. MS (ESI): 249.1, 251.0 [M+H]$^+$.

Example 13

(4-Chloro-phenyl)-(3-isopropyl-3H-imidazol-4-yl)-methanone

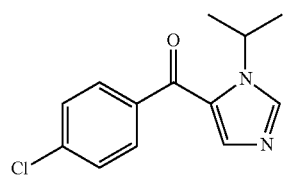 [SMILES: CC(C)n1cncc1C(=O)c1ccc(Cl)cc1]

was synthesized in analogy to example 6, but using in step 1 4-chloro-benzaldehyde instead of 4-formyl-benzonitrile, as colorless oil. MS (ESI): 249.1, 250.8 [M+H]$^+$.

Example 14

(3,4-Dichloro-phenyl)-(3-isopropyl-3H-imidazol-4-yl)-methanone

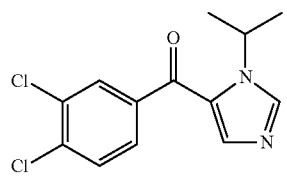 [SMILES: CC(C)n1cncc1C(=O)c1ccc(Cl)c(Cl)c1]

was synthesized in analogy to example 6, but using in step 1 3,4-dichloro-benzaldehyde instead of 4-formyl-benzonitrile, as colorless oil. MS (ESI): 283.0, 285.0, 287.0 [M+H]$^+$.

Example 15

(3,4-Dichloro-phenyl)-(3-ethyl-3H-imidazol-4-yl)-methanone

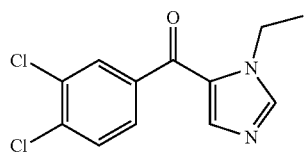 [SMILES: CCn1cncc1C(=O)c1ccc(Cl)c(Cl)c1]

was synthesized in analogy to example 14, but using in step 1 1-ethyl-5-iodo-1H-imidazole (intermediate 1a) instead of 5-iodo-1-isopropyl-1H-imidazole (intermediate 1b), as white solid. MS (ESI): 269.1, 271.1, 273.1 [M+H]$^+$.

Example 16

4-(3-sec-Butyl-3H-imidazole-4-carbonyl)-benzonitrile

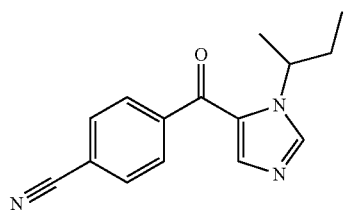 [SMILES: CCC(C)n1cncc1C(=O)c1ccc(C#N)cc1]

was prepared in analogy to example 2, but starting the sequence with 1-sec-butyl-5-iodo-1H-imidazole (intermediate 1d) as white solid. MS (ESI): 254.1 [M+H]$^+$.

Example 17

4-(3-sec-Butyl-3H-imidazole-4-carbonyl)-benzonitrile

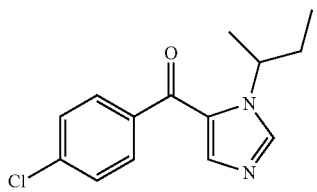 [SMILES: CCC(C)n1cncc1C(=O)c1ccc(Cl)cc1]

was synthesized in analogy to example 16, but using in step 1 4-chloro-benzaldehyde instead of 4-formyl-benzonitrile, as yellow oil. MS (ESI): 263.1, 265.0 [M+H]$^+$.

Example 18

Step 1

4-[(3-Cyclopropyl-3H-imidazol-4-yl)-hydroxymethyl]-benzonitrile

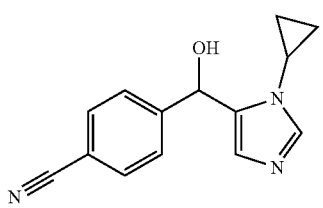 [SMILES: N#Cc1ccc(C(O)c2cncn2C2CC2)cc1]

In a 10 mL two-necked flask, 5-bromo-1-cyclopropyl-1H-imidazole (intermediate 1c', 107 mg, 572 µmol, Eq: 1.00) was combined with DCM (3 ml) to give a colorless solution. Isopropyl magnesium chloride, lithium chloride complex (484 µl, 629 µmol, Eq: 1.1) was added within 2 min (white precipitate). After stirring for 80 min., the reaction flask was cooled to 0° C., and a solution of 4-formylbenzonitrile (90.0 mg, 686 µmol, Eq: 1.2) in DCM (2 ml) was added dropwise. The reaction was allowed to proceed at rt for 2 h when TLC showed that the reaction was complete. Work up: The reaction mixture was quenched with 3 ml sat. NH$_4$Cl, then poured into 6 ml sat. NaHCO$_3$ and extracted with DCM (2×25 ml). The organic layers were washed with brine, combined, dried over Na$_2$SO$_4$, and concentrated i. V. The crude material was purified by flash chromatography (silica gel, 20 g, 2% to 10% MeOH in DCM) to yield 81 mg of the title compound as white foam. MS (ESI): 240.1 [M+H]$^+$.

Step 2

4-(3-Cyclopropyl-3H-imidazole-4-carbonyl)-benzonitrile

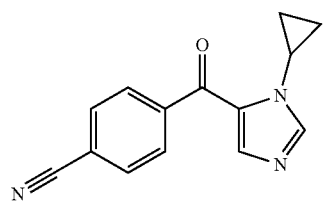 [SMILES: N#Cc1ccc(C(=O)c2cncn2C2CC2)cc1]

In a 25 mL round-bottomed flask, the above prepared 4-((1-cyclopropyl-1H-imidazol-5-yl)(hydroxy)methyl)benzonitrile (78 mg, 326 µmol, Eq: 1.00) was combined with DCM (6 ml) to give a colorless solution. Manganese dioxide (567 mg, 6.52 mmol, Eq: 20) was added and the reaction mixture was vigorously stirred at rt. TLC after 2 h indicated the absence of starting material. Work up: The reaction mixture was filtered through celite, washed with DCM and concentrated. The crude product was purified by flash chromatography (silica gel, 10 g, 0% to 5% MeOH in DCM) to provide 62 mg of the title compound as white semisolid. MS (ESI): 238.0 [M+H]$^+$.

Example 19

(4-Chloro-phenyl)-(3-cyclopropyl-3H-imidazol-4-yl)-methanone

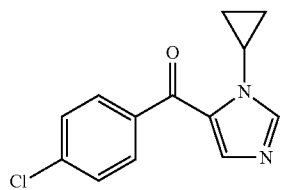 [SMILES: O=C(c1ccc(Cl)cc1)c1cncn1C1CC1]

was synthesized in analogy to example 18, but using in step 1 4-chloro-benzaldehyde instead of 4-formyl-benzonitrile, as colorless oil. MS (ESI): 247.1, 249.0 [M+H]$^+$.

Example 20

4-[3-(2,2,2-Trifluoro-ethyl)-3H-imidazole-4-carbonyl]-benzonitrile

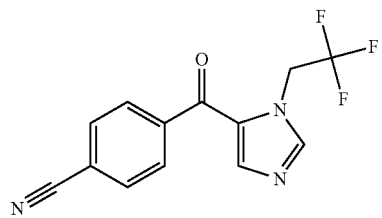 [SMILES: N#Cc1ccc(C(=O)c2cncn2CC(F)(F)F)cc1]

was prepared in analogy to example 2, but starting the sequence with 5-iodo-1-(2,2,2-trifluoroethyl)-1H-imidazole (intermediate 1e) as colorless oil. MS (ESI): 280.0 [M+H]$^+$.

Example 21

3-(3-Methyl-3H-imidazole-4-carbonyl)-benzonitrile

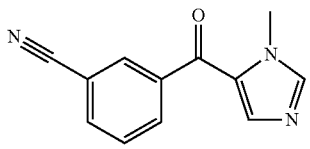 [SMILES: Cn1cncc1C(=O)c1cccc(C#N)c1]

was synthesized in analogy to example 1, but using in step 1 3-formyl-benzonitrile instead of 4-chlorobenzaldehyde, as white semisolid. MS (ESI): 212.0 [M+H]$^+$.

Example 22

(3-Chloro-phenyl)-(3-methyl-3H-imidazol-4-yl)-methanone

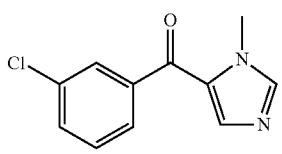

was synthesized in analogy to example 1, but using in step 1 3-chlorobenzaldehyde instead of 4-chlorobenzaldehyde, as white semisolid. MS (ESI): 221.1, 223.1 [M+H]$^+$.

Example 23

(4-Fluoro-phenyl)-(3-methyl-3H-imidazol-4-yl)-methanone

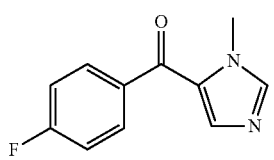

was synthesized in analogy to example 1, but using in step 1 4-fluorobenzaldehyde instead of 4-chlorobenzaldehyde, as white semisolid. MS (ESI): 205.1 [M+H]$^+$.

Example 24

(3-Fluoro-phenyl)-(3-methyl-3H-imidazol-4-yl)-methanone

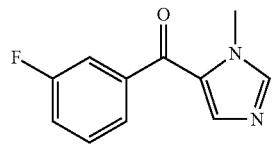

was synthesized in analogy to example 1, but using in step 1 3-fluorobenzaldehyde instead of 4-chlorobenzaldehyde, as white semisolid. MS (ESI): 205.1 [M+H]$^+$.

Example 25

1-Methyl-6-(3-methyl-3H-imidazole-4-carbonyl)-3,4-dihydro-1H-quinolin-2-one

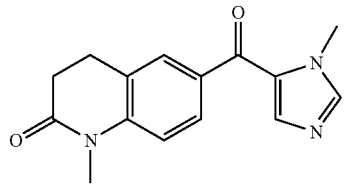 [SMILES: CN1C(=O)CCc2cc(C(=O)c3cncn3C)ccc21]

was synthesized in analogy to example 1, but using in step 1 1-methyl-2-oxo-1,2,3,4-tetrahydro-quinoline-6-carbaldehyde (intermediate 2a) instead of 4-chlorobenzaldehyde, as white solid. MS (ESI): 270.2 [M+H]$^+$.

Example 26

6-(3-Ethyl-3H-imidazole-4-carbonyl)-1-methyl-3,4-dihydro-1H-quinolin-2-one

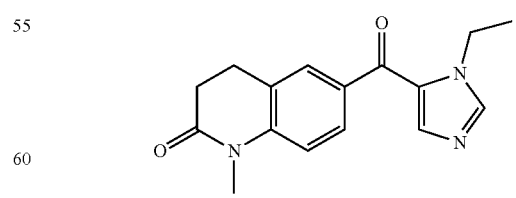

was prepared in analogy to example 25, but starting the sequence with 1-ethyl-5-iodo-1H-imidazole (intermediate 1a) instead of 5-iodo-1-methyl-1H-imidazole, as white solid. MS (ESI): 284.1 [M+H]$^+$.

Example 27

6-(3-Isopropyl-3H-imidazole-4-carbonyl)-1-methyl-3,4-dihydro-1H-quinolin-2-one

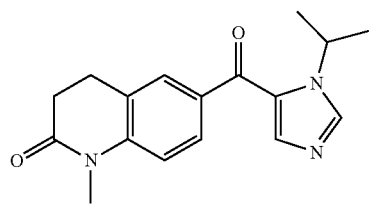 [SMILES: CC(C)n1cncc1C(=O)c1ccc2c(c1)CCC(=O)N2C]

was prepared in analogy to example 25, but starting the sequence with 5-iodo-1-isopropyl-1H-imidazole (intermediate 1b) instead of 5-iodo-1-methyl-1H-imidazole, as colorless oil. MS (ESI): 298.3 [M+H]$^+$.

Example 28

(3-sec-Butyl-3H-imidazol-4-yl)-(3-chloro-phenyl)-methanone

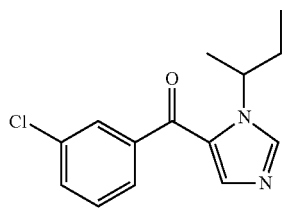 [SMILES: CCC(C)n1cncc1C(=O)c1cccc(Cl)c1]

was prepared in analogy to example 22, but starting the sequence with 1-sec-butyl-5-iodo-1H-imidazole (intermediate 1d) instead of 5-iodo-1-methyl-1H-imidazole, as colorless oil. MS (ESI): 263.1, 265.1 [M+H]$^+$.

Example 29

(4-Ethynyl-phenyl)-(3-methyl-3H-imidazol-4-yl)-methanone

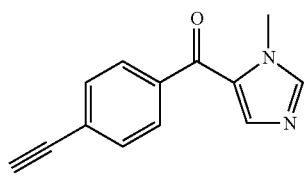 [SMILES: C#Cc1ccc(C(=O)c2cncn2C)cc1]

was synthesized in analogy to example 1, but using in step 1 4-ethynyl-benzaldehyde instead of 4-chlorobenzaldehyde, as off-white powder. MS (ESI): 211.0 [M+H]$^+$.

Example 30

(4-tert-Butyl-phenyl)-(3-methyl-3H-imidazol-4-yl)-methanone

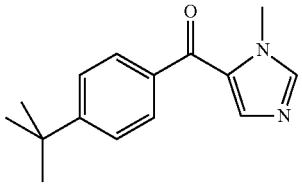 [SMILES: Cn1cncc1C(=O)c1ccc(C(C)(C)C)cc1]

was synthesized in analogy to example 1, but using in step 1 4-tert-butyl-benzaldehyde instead of 4-chlorobenzaldehyde, as off-white powder. MS (ESI): 243.2 [M+H]$^+$.

Example 31

(3-Methyl-3H-imidazol-4-yl)-(4-trifluoromethyl-phenyl)-methanone

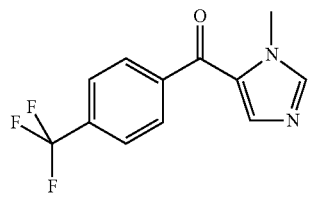 [SMILES: Cn1cncc1C(=O)c1ccc(C(F)(F)F)cc1]

was synthesized in analogy to example 1, but using in step 1 4-trifluoromethyl-benzaldehyde instead of 4-chlorobenzaldehyde, as light yellow powder. MS (ESI): 255.0 [M+H]$^+$.

Example 32

(3-Chloro-4-fluoro-phenyl)-(3-methyl-3H-imidazol-4-yl)-methanone

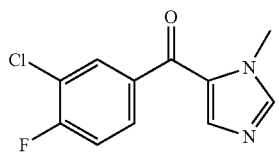

was synthesized in analogy to example 1, but using in step 1 3-chloro-4-fluoro-benzaldehyde instead of 4-chlorobenzaldehyde, as white solid. MS (ESI): 239.0, 241.2 [M+H]$^+$.

Example 33

(3-Chloro-4-fluoro-phenyl)-(3-ethyl-3H-imidazol-4-yl)-methanone

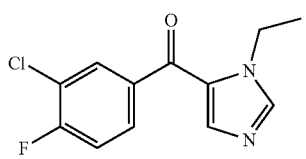 [SMILES: CCn1cncc1C(=O)c1ccc(F)c(Cl)c1]

was prepared in analogy to example 32, but starting the sequence with 1-ethyl-5-iodo-1H-imidazole (intermediate 1a) instead of 5-iodo-1-methyl-1H-imidazole, as white solid. MS (ESI): 253.1, 255.2 [M+H]+.

Example 34

(4-Chloro-3-fluoro-phenyl)-(3-ethyl-3H-imidazol-4-yl)-methanone

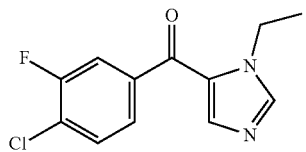 [SMILES: CCn1cncc1C(=O)c1ccc(Cl)c(F)c1]

was synthesized in analogy to example 33, but using in step 1 4-chloro-3-fluoro-benzaldehyde instead of 3-chloro-4-fluoro-benzaldehyde, as white solid. MS (ESI): 253.1, 255.2 [M+H]+.

Example 35

(4-tert-Butyl-phenyl)-(3-ethyl-3H-imidazol-4-yl)-methanone

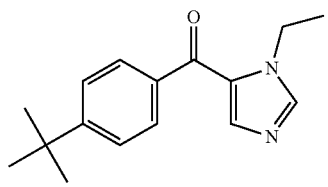 [SMILES: CCn1cncc1C(=O)c1ccc(C(C)(C)C)cc1]

was synthesized in analogy to example 30, but starting the sequence with 1-ethyl-5-iodo-1H-imidazole (intermediate 1a) instead of 5-iodo-1-methyl-1H-imidazole, as colorless oil. MS (ESI): 257.2 [M+H]+.

Example 36

(3-Ethyl-3H-imidazol-4-yl)-(4-trifluoromethyl-phenyl)-methanone

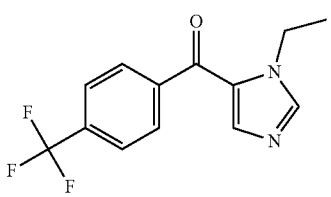 [SMILES: CCn1cncc1C(=O)c1ccc(C(F)(F)F)cc1]

was synthesized in analogy to example 35, but using in step 1 4-trifluoromethyl-benzaldehyde instead of 4-tert-butyl-benzaldehyde, as off-white semisolid. MS (ESI): 269.1 [M+H]+.

Example 37

3-(3-sec-Butyl-3H-imidazole-4-carbonyl)-benzonitrile

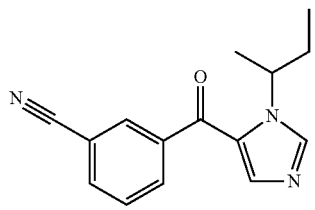 [SMILES: CCC(C)n1cncc1C(=O)c1cccc(C#N)c1]

was synthesized in analogy to example 28, but using in step 3-formyl-benzonitrile instead of 3-chlorobenzaldehyde, as colorless oil. MS (ESI): 254.1 [M+H]+.

Example 38

(3-Chloro-4-fluoro-phenyl)-(3-isopropyl-3H-imidazol-4-yl)-methanone

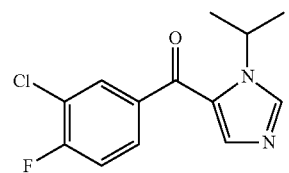 [SMILES: CC(C)n1cncc1C(=O)c1ccc(F)c(Cl)c1]

was prepared in analogy to example 32, but starting the sequence with 5-iodo-1-isopropyl-1H-imidazole (intermediate 1b) instead of 5-iodo-1-methyl-1H-imidazole, as colorless oil. MS (ESI): 267.0, 269.1 [M+H]+.

Example 39

(4-Chloro-3-fluoro-phenyl)-(3-isopropyl-3H-imidazol-4-yl)-methanone

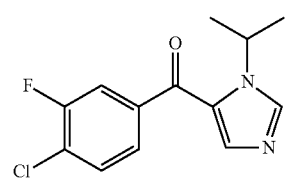 [SMILES: CC(C)n1cncc1C(=O)c1ccc(Cl)c(F)c1]

was prepared in analogy to example 38, but using in step 1 4-chloro-3-fluoro-benzaldehyde instead of 3-chloro-4-fluoro-benzaldehyde, as colorless oil. MS (ESI): 267.0, 269.1 [M+H]+.

Example 40

(4-Chloro-3-fluoro-phenyl)-(3-cyclopropyl-3H-imidazol-4-yl)-methanone

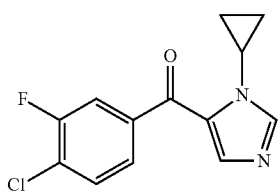 [SMILES: O=C(c1ccc(Cl)c(F)c1)c1cncn1C1CC1]

was prepared in analogy to example 18, but using in step 1 4-chloro-3-fluoro-benzaldehyde instead of 4-formylbenzonitrile, as light yellow oil. MS (ESI): 265.0, 266.8 [M+H]$^+$.

Example 41

(3-Chloro-4-fluoro-phenyl)-(3-cyclopropyl-3H-imidazol-4-yl)-methanone

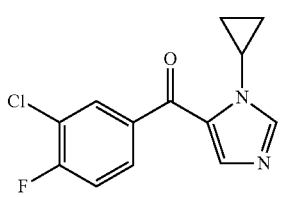 [SMILES: O=C(c1ccc(F)c(Cl)c1)c1cncn1C1CC1]

was prepared in analogy to example 40, but using in step 1 3-chloro-4-fluoro-benzaldehyde instead of 4-chloro-3-fluoro-benzaldehyde, as light yellow oil. MS (ESI): 265.0, 266.9 [M+H]$^+$.

Example 42

2-Chloro-4-(3-methyl-3H-imidazole-4-carbonyl)-benzonitrile

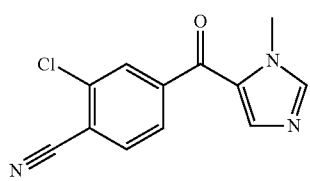 [SMILES: Cn1cncc1C(=O)c1ccc(C#N)c(Cl)c1]

was prepared in analogy to example 1, but using in step 1 2-chloro-4-formylbenzonitrile (intermediate 2b) instead of 4-chlorobenzaldehyde, as white solid. MS (ESI): 246.1, 248.1 [M+H]$^+$.

Example 43

(3-Methyl-3H-imidazol-4-yl)-(4-methylsulfanyl-phenyl)-methanone

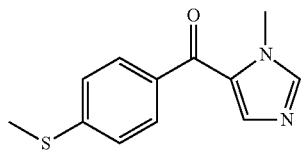 [SMILES: CSc1ccc(C(=O)c2cncn2C)cc1]

was prepared in analogy to example 1, but using in step 1 4-methylsulfanyl-benzaldehyde instead of 4-chlorobenzaldehyde, as white semisolid. MS (ESI): 233.0 [M+H]$^+$.

Example 44

Benzo[b]thiophen-5-yl-(3-methyl-3H-imidazol-4-yl)-methanone

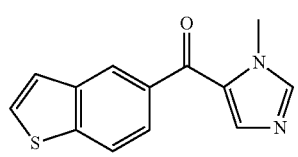 [SMILES: Cn1cncc1C(=O)c1ccc2sccc2c1]

was prepared in analogy to example 1, but using in step 1 benzo[b]thiophene-5-carbaldehyde instead of 4-chlorobenzaldehyde, as white solid. MS (ESI): 243.1 [M+H]$^+$.

Example 45

2-Fluoro-5-(3-methyl-3H-imidazole-4-carbonyl)-benzonitrile

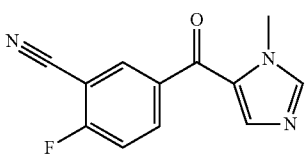 [SMILES: Cn1cncc1C(=O)c1ccc(F)c(C#N)c1]

was prepared in analogy to example 1, but using in step 1 2-fluoro-5-formyl-benzonitrile instead of 4-chlorobenzaldehyde, as white solid. MS (ESI): 230.2 [M+H]$^+$.

Example 46

2-Chloro-4-(3-ethyl-3H-imidazole-4-carbonyl)-benzonitrile

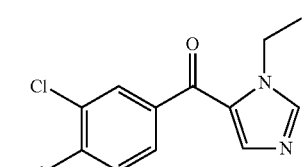

was synthesized in analogy to example 42, but starting the sequence with 1-ethyl-5-iodo-1H-imidazole (intermediate 1a) instead of 5-iodo-1-methyl-1H-imidazole, as white solid. MS (ESI): 260.0, 262.0 [M+H]+.

Example 47

(4-Methanesulfonyl-phenyl)-(3-methyl-3H-imidazol-4-yl)-methanone

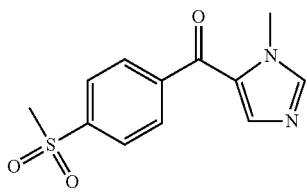 [SMILES: Cn1cncc1C(=O)c1ccc(S(C)(=O)=O)cc1]

In a 10 mL round-bottomed flask, the above prepared (1-methyl-1H-imidazol-5-yl)(4-(methylthio)phenyl)methanone (example 43, 60 mg, 258 µmol, Eq: 1.00) was combined with DCM (3 ml) to give a colorless solution. mCPBA (159 mg, 646 µmol, Eq: 2.5) was added while cooling with an ice bath, and the reaction mixture stirred at ambient temperature for 2 h when TLC indicated that the reaction was complete. Work up: the reaction mixture was quenched with Na$_2$SO$_3$ sol. 10 mL and extracted with DCM (2×15 mL). The organic layers were combined, dried over Na$_2$SO$_4$, and concentrated i. V. The crude material was purified by flash chromatography (silica gel, 10 g, 0% to 5% MeOH in DCM) to yield 53 mg of the title compound as white semisolid. MS (ESI): 265.0 [M+H]+.

Example 48

(3-Ethyl-3H-imidazol-4-yl)-(4-ethynyl-phenyl)-methanone

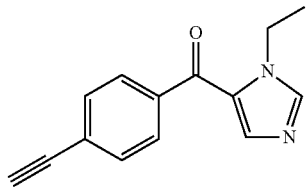 [SMILES: C#Cc1ccc(C(=O)c2cncn2CC)cc1]

was synthesized in analogy to example 29, but starting the sequence with 1-ethyl-5-iodo-1H-imidazole (intermediate 1a) instead of 5-iodo-1-methyl-1H-imidazole, as light yellow oil. MS (ESI): 225.1 [M+H]+.

Example 49

2-Chloro-4-(3-isopropyl-3H-imidazole-4-carbonyl)-benzonitrile

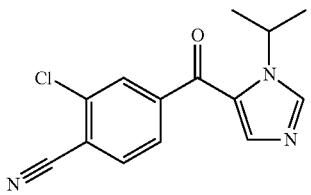 [SMILES: CC(C)n1cncc1C(=O)c1ccc(C#N)c(Cl)c1]

was synthesized in analogy to example 42, but starting the sequence with 5-iodo-1-isopropyl-1H-imidazole (intermediate 1b) instead of 5-iodo-1-methyl-1H-imidazole, as white foam. MS (ESI): 274.1, 276.1 [M+H]+.

Example 50

(3-Methoxy-4-methylsulfanyl-phenyl)-(3-methyl-3H-imidazol-4-yl)-methanone

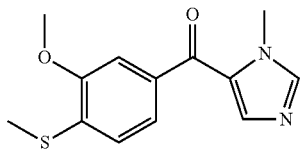 [SMILES: COc1cc(C(=O)c2cncn2C)ccc1SC]

was prepared in analogy to example 1, but using in step 1 3-methoxy-4-methylsulfanyl-benzaldehyde instead of 4-chlorobenzaldehyde, as white solid. MS (ESI): 263.1 [M+H]+.

Example 51

(4-Ethylsulfanyl-phenyl)-(3-methyl-3H-imidazol-4-yl)-methanone

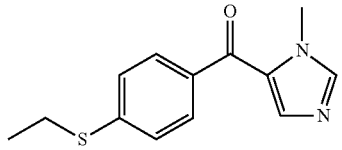 [SMILES: CCSc1ccc(C(=O)c2cncn2C)cc1]

was prepared in analogy to example 1, but using in step 1 4-ethylsulfanyl-benzaldehyde instead of 4-chlorobenzaldehyde, as white solid. MS (ESI): 247.2 [M+H]+.

Example 52

(4-Methanesulfonyl-3-methoxy-phenyl)-(3-methyl-3H-imidazol-4-yl)-methanone

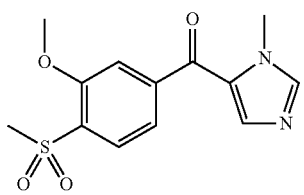 [SMILES: COc1cc(C(=O)c2cncn2C)ccc1S(C)(=O)=O]

was synthesized an analogy to example 47, but using (3-methoxy-4-methylsulfanyl-phenyl)-(3-methyl-3H-imidazol-4-yl)-methanone (example 50) as starting material, as white foam. MS (ESI): 295.1 [M+H]+.

Example 53

(4-Ethanesulfonyl-phenyl)-(3-methyl-3H-imidazol-4-yl)-methanone

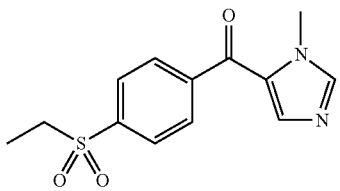 [SMILES: CCS(=O)(=O)c1ccc(C(=O)c2cncn2C)cc1]

was synthesized an analogy to example 47, but using (4-ethylsulfanyl-phenyl)-(3-methyl-3H-imidazol-4-yl)-methanone (example 51) as starting material, as white semisolid. MS (ESI): 279.0 [M+H]$^+$.

Example 54

Step 1

(4-Ethynyl-phenyl)-(3-isopropyl-3H-imidazol-4-yl)-methanol

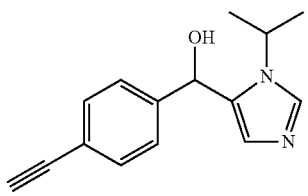 [SMILES: C#Cc1ccc(C(O)c2cncn2C(C)C)cc1]

In a 10 mL round-bottomed flask, 5-bromo-1-isopropyl-1H-imidazole (intermediate 1b', 146.2 mg, 773 µmol, Eq: 1.00) was combined with DCM (3 ml) to give a light yellow solution. Isopropyl magnesium chloride, lithium chloride complex (654 µl, 851 µmol, Eq: 1.1) was added and metallation allowed to proceed for 1 h at RT. The reaction mixture was cooled down to 0° C., 4-ethynylbenzaldehyde (111 mg, 851 µmol, Eq: 1.1) and DCM (2 ml) was added, and the reaction was allowed to proceed for 1 h. TLC indicated the absence of starting material. Work up: The reaction mixture was poured into 10 mL sat. NaHCO$_3$ and 10 ml H$_2$O and extracted with EtOAc (2×25 mL). The organic layers were combined, dried over Na$_2$SO$_4$, and concentrated i. V. The crude product was eventually purified by flash chromatography (silica gel, 20 g, 2% to 10% MeOH in DCM) to afford 124 mg of the title compound as light yellow semisolid. MS (ESI): 241.2 [M+H]$^+$.

Step 2

(4-Ethynyl-phenyl)-(3-isopropyl-3H-imidazol-4-yl)-methanone

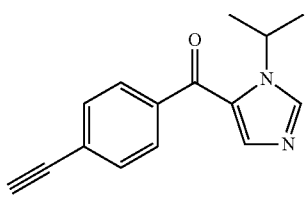 [SMILES: C#Cc1ccc(C(=O)c2cncn2C(C)C)cc1]

In a 10 mL round-bottomed flask, the above prepared (4-ethynylphenyl)(1-isopropyl-1H-imidazol-5-yl)methanol (106 mg, 441 µmol, Eq: 1.00) was combined with DCM (6 ml) to give a light yellow solution. Manganese dioxide (767 mg, 8.82 mmol, Eq: 20) was added and the reaction mixture vigorously stirred for 3 h at RT. Work up: The reaction mixture was filtered through celite and thoroughly washed with DCM; evaporation of the solvent i. V., followed by flash chromatography (silica gel, 10 g, 0% to 5% MeOH in DCM) gave 102 mg of the title compound as colorless oil. MS (ESI): 239.0 [M+H]$^+$.

Example 55

N-Methyl-N-[4-(3-methyl-3H-imidazole-4-carbonyl)-phenyl]-acetamide

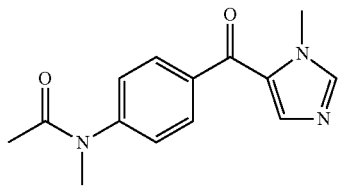 [SMILES: CC(=O)N(C)c1ccc(C(=O)c2cncn2C)cc1]

was prepared in analogy to example 1, but using in step 1 N-(4-formyl-phenyl)-N-methyl-acetamide instead of 4-chlorobenzaldehyde, as white solid. MS (ESI): 258.2 [M+H]$^+$.

Example 56

Step 1

3-[(3-Ethyl-3H-imidazol-4-yl)-hydroxy-methyl]-benzonitrile

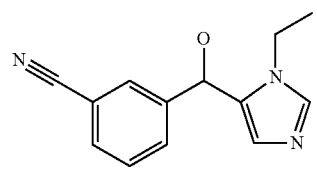 [SMILES: CCn1cncc1C(O)c1cccc(C#N)c1]

In a 25 mL round-bottomed flask, 5-bromo-1-ethyl-1H-imidazole (intermediate 1a', 170 mg, 971 µmol, Eq: 1.00) was combined with DCM (4 ml) to give a colorless solution. Isopropyl magnesium chloride, lithium chloride complex (822 µl, 1.07 mmol, Eq: 1.1) was added, and the reaction mixture was stirred at rt for 1 h. After cooling to 0° C., a solution of 3-formylbenzonitrile (153 mg, 1.17 mmol, Eq: 1.2) in DCM (3 ml) was dropwise added, and the mixture was stirred at rt for another 3 h when TLC showed that the reaction was finished. Work up: the reaction mixture was quenched with 2 ml sat. NH$_4$Cl and extracted with sat. NaHCO$_3$/DCM. The combined organic layers were dried over Na$_2$SO$_4$ and concentrated i. V. The crude product was purified by flash chromatography (silica gel, 20 g, 2% to 10% MeOH in DCM) to generate 120 mg of the title compound as off-white semisolid.

Step 2

3-(3-Ethyl-3H-imidazole-4-carbonyl)-benzonitrile

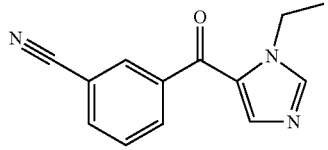 [SMILES: CCn1cncc1C(=O)c1cccc(C#N)c1]

In a 25 mL round-bottomed flask, the above prepared 3-((1-ethyl-1H-imidazol-5-yl)(hydroxy)methyl)benzonitrile (111 mg, 488 µmol, Eq: 1.00) was combined with DCM (10 ml) to give a colorless solution. Manganese dioxide (849 mg, 9.77 mmol, Eq: 20) was added and the reaction mixture was vigorously stirred for 3 hr at rt. Work up: the reaction mixture was filtered through celite, carefully washed with DCM and concentrated i. V. The crude product was purified by flash chromatography (silica gel, 10 g, 0% to 5% MeOH in DCM) to provide 77 mg of the title compound as white semisolid. MS (ESI): 226.2 [M+H]$^+$.

Example 57

3-(3-Isopropyl-3H-imidazole-4-carbonyl)-benzonitrile

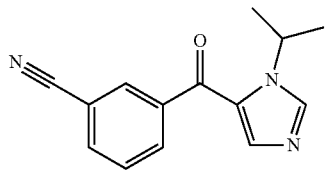 [SMILES: CC(C)n1cncc1C(=O)c1cccc(C#N)c1]

was prepared in analogy to example 54, but using in step 1 3-formyl-benzonitrile instead of 4-ethynylbenzaldehyde, as colorless oil. MS (ESI): 240.1 [M+H]$^+$.

Example 58

3-(3-Cyclopropyl-3H-imidazole-4-carbonyl)-benzonitrile

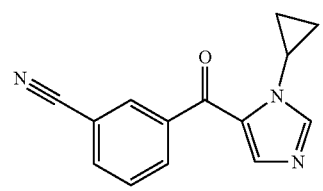 [SMILES: N#Cc1cccc(C(=O)c2cncn2C2CC2)c1]

was prepared in analogy to example 18, but using in step 1 3-formyl-benzonitrile instead of 4-formylbenzonitrile, as white semisolid. MS (ESI): 238.1 [M+H]$^+$.

Example 59

N-[4-(3-Isopropyl-3H-imidazole-4-carbonyl)-phenyl]-N-methyl-acetamide

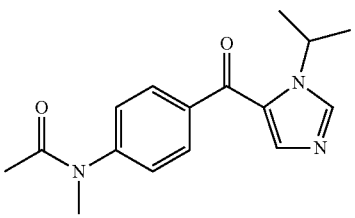 [SMILES: CC(=O)N(C)c1ccc(C(=O)c2cncn2C(C)C)cc1]

was synthesized in analogy to example 6, but using in step 1 N-(4-formyl-phenyl)-N-methyl-acetamide instead of 4-formyl-benzonitrile, as light yellow solid. MS (ESI): 286.0 [M+H]$^+$.

Example 60

(3-Ethyl-3H-imidazol-4-yl)-(3-methoxy-4-methylsulfanyl-phenyl)-methanone

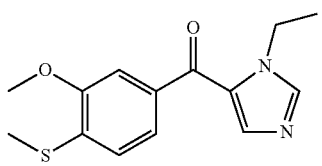 [SMILES: CCn1cncc1C(=O)c1ccc(SC)c(OC)c1]

was synthesized in analogy to example 56, but using in step 1 3-methoxy-4-methylsulfanyl-benzaldehyde instead of 3-formylbenzonitrile, as white foam. MS (ESI): 277.1 [M+H]$^+$.

Example 61

(3-Isopropyl-3H-imidazol-4-yl)-(3-methoxy-4-methylsulfanyl-phenyl)-methanone

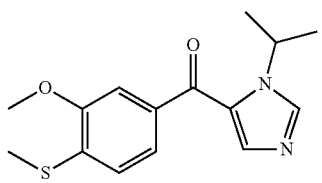 [SMILES: COc1cc(C(=O)c2cncn2C(C)C)ccc1SC]

was synthesized in analogy to example 54, but using in step 1 3-methoxy-4-methylsulfanyl-benzaldehyde instead of 4-ethynylbenzaldehyde, as colorless oil. MS (ESI): 291.1 [M+H]$^+$.

Example 62

(3-Cyclopropyl-3H-imidazol-4-yl)-(3-methoxy-4-methylsulfanyl-phenyl)-methanone

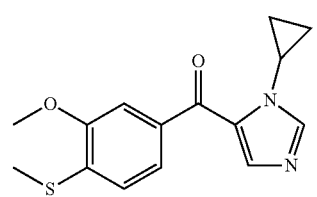 [SMILES: COc1cc(C(=O)c2cncn2C2CC2)ccc1SC]

was synthesized in analogy to example 18, but using in step 1 3-methoxy-4-methylsulfanyl-benzaldehyde instead of 4-formylbenzonitrile, as white foam. MS (ESI): 289.0 [M+H]$^+$.

Example 63

5-(3-Ethyl-3H-imidazole-4-carbonyl)-2-fluoro-benzonitrile

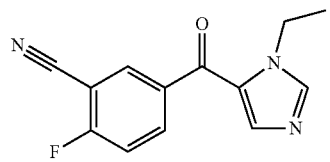 [SMILES: CCn1cncc1C(=O)c1ccc(F)c(C#N)c1]

was synthesized in analogy to example 56, but using in step 1 2-fluoro-5-formyl-benzonitrile instead of 3-formylbenzonitrile, as white solid. MS (ESI): 244.2 [M+H]$^+$.

Example 64

2-Fluoro-5-(3-isopropyl-3H-imidazole-4-carbonyl)-benzonitrile

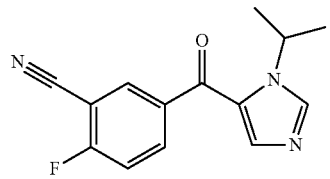 [SMILES: CC(C)n1cncc1C(=O)c1ccc(F)c(C#N)c1]

was synthesized in analogy to example 54, but using in step 1 2-fluoro-5-formyl-benzonitrile instead of 4-ethynylbenzaldehyde, as colorless oil. MS (ESI): 258.1 [M+H]$^+$.

Example 65

5-(3-sec-Butyl-3H-imidazole-4-carbonyl)-2-fluoro-benzonitrile

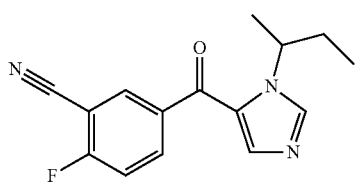 [SMILES: CCC(C)n1cncc1C(=O)c1ccc(F)c(C#N)c1]

was synthesized in analogy to example 64, but starting the sequence with 5-bromo-1-sec-butyl-1H-imidazole (intermediate 1d') instead of 5-bromo-1-isopropyl-1H-imidazole, as colorless oil. MS (ESI): 272.1 [M+H]$^+$.

Example 66

5-(3-Cyclopropyl-3H-imidazole-4-carbonyl)-2-fluoro-benzonitrile

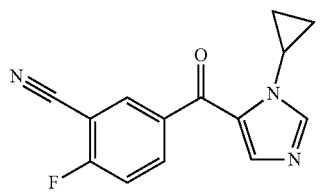 [SMILES: N#Cc1cc(C(=O)c2cncn2C2CC2)ccc1F]

was prepared in analogy to example 64, but starting the sequence with 5-bromo-1-cyclopropyl-1H-imidazole (intermediate 1c') instead of 5-bromo-1-isopropyl-1H-imidazole, as off-white solid. MS (ESI): 256.1 [M+H]$^+$.

Example 67

N-[4-(3-Ethyl-3H-imidazole-4-carbonyl)-phenyl]-N-methyl-acetamide

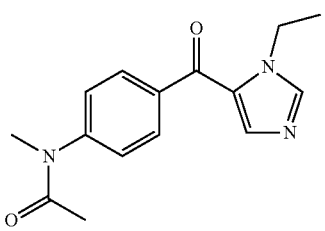 [SMILES: CCn1cncc1C(=O)c1ccc(N(C)C(C)=O)cc1]

was synthesized in analogy to example 55, but starting the sequence 5-bromo-1-ethyl-1H-imidazole (intermediate 1a') instead of 5-iodo-1-methyl-1H-imidazole, as white solid. MS (ESI): 272.3 [M+H]$^+$.

Example 68

(4-Bromo-phenyl)-(3-methyl-3H-imidazol-4-yl)-methanone

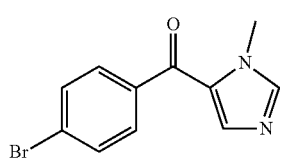

was prepared in analogy to example 1, but using in step 1 4-bromobenzaldehyde instead of 4-chlorobenzaldehyde, as white solid. MS (ESI): 265.0, 266.9 [M+H]$^+$.

Example 69

(3-Ethyl-3H-imidazol-4-yl)-(4-ethylsulfanyl-phenyl)-methanone

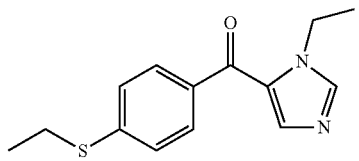 [SMILES: CCSc1ccc(C(=O)c2cncn2CC)cc1]

was prepared in analogy to example 56, but using in step 1 4-ethylsulfanyl-benzaldehyde instead of 3-formylbenzonitrile, as white semisolid. MS (ESI): 261.2 [M+H]$^+$.

Example 70

(3-Cyclopropyl-3H-imidazol-4-yl)-(4-ethylsulfanyl-phenyl)-methanone

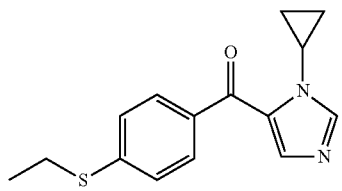 [SMILES: CCSc1ccc(C(=O)c2cncn2C2CC2)cc1]

was prepared in analogy to example 18, but using in step 1 4-ethylsulfanyl-benzaldehyde instead of 4-formylbenzonitrile, as white semisolid. MS (ESI): 273.3 [M+H]$^+$.

Example 71

(4-Ethylsulfanyl-phenyl)-(3-isopropyl-3H-imidazol-4-yl)-methanone

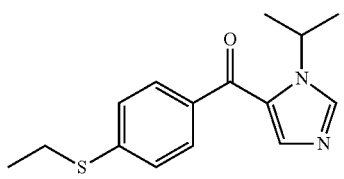 [SMILES: CCSc1ccc(C(=O)c2cncn2C(C)C)cc1]

was prepared in analogy to example 54, but using in step 1 4-ethylsulfanyl-benzaldehyde instead of 4-ethynylbenzaldehyde, as white semisolid. MS (ESI): 275.1 [M+H]$^+$.

Example 72

(4-Bromo-phenyl)-(3-isopropyl-3H-imidazol-4-yl)-methanone

was prepared in analogy to example 54, but using in step 1 4-bromobenzaldehyde instead of 4-ethynylbenzaldehyde, as colorless oil. MS (ESI): 292.9, 295.0 [M+H]$^+$.

Example 73

(3-Methyl-3H-imidazol-4-yl)-(4-trifluoromethylsulfanyl-phenyl)-methanone

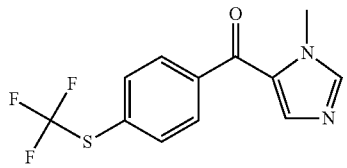 [SMILES: Cn1cncc1C(=O)c1ccc(SC(F)(F)F)cc1]

was prepared in analogy to example 1, but using in step 1 4-trifluoromethylsulfanyl-benzaldehyde instead of 4-chlorobenzaldehyde, as white semisolid. MS (ESI): 287.0 [M+H]$^+$.

Example 74

(3-Ethyl-3H-imidazol-4-yl)-(4-trifluoromethylsulfanyl-phenyl)-methanone

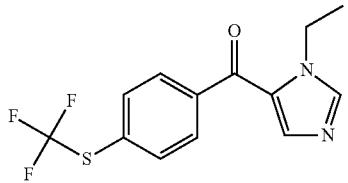 [SMILES: CCn1cncc1C(=O)c1ccc(SC(F)(F)F)cc1]

was synthesized in analogy to example 56, but using in step 1 4-trifluoromethylsulfanyl-benzaldehyde instead of 3-formylbenzonitrile, as colorless oil. MS (ESI): 301.1 [M+H]$^+$.

Example 75

(3-Isopropyl-3H-imidazol-4-yl)-(4-trifluoromethylsulfanyl-phenyl)-methanone

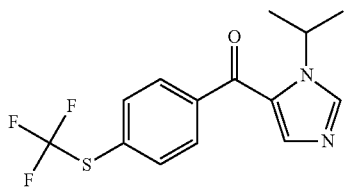 [SMILES: CC(C)n1cncc1C(=O)c1ccc(SC(F)(F)F)cc1]

was prepared in analogy to example 54, but using in step 1 4-trifluoromethylsulfanyl-benzaldehyde instead of 4-ethynylbenzaldehyde, as colorless oil. MS (ESI): 315.0 [M+H]$^+$.

Example 76

[3-(1-Ethyl-propyl)-3H-imidazol-4-yl]-(4-trifluoromethylsulfanyl-phenyl)-methanone

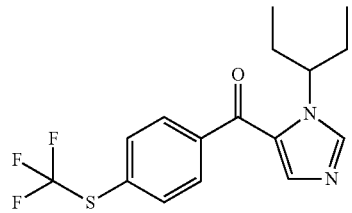 [SMILES: CCC(CC)n1cncc1C(=O)c1ccc(SC(F)(F)F)cc1]

was prepared in analogy to example 75, but starting the sequence with 5-bromo-1-(1-ethyl-propyl)-1H-imidazole (intermediate 1f) instead of 5-bromo-1-isopropyl-1H-imidazole, as colorless oil. MS (ESI): 343.1 [M+H]+.

Example 77

Step 1

3-(3-Chloro-4-cyano-phenyl)-3H-imidazole-4-carboxylic acid ethyl ester

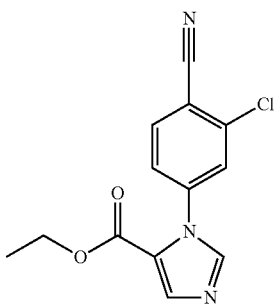 [SMILES: CCOC(=O)c1cncn1-c1ccc(C#N)c(Cl)c1]

In a 50 mL round-bottomed flask, 4-amino-2-chlorobenzonitrile (1 g, 6.55 mmol, Eq: 1.00) was combined with methanol (35 ml) to give a light yellow solution. Ethyl 2-oxoacetate 50% in toluene (2.01 g, 1.95 ml, 9.83 mmol, Eq: 1.5) was added, and the reaction mixture was stirred over night at reflux. Work up: The crude reaction mixture was concentrated i. v., the residue dissolved in AcOEt and washed twice with H$_2$O and brine. After drying over Na$_2$SO$_4$ and evaporation of all solvents, one obtained the crude product as light brown oil which was used directly without further purification. It was dissolved in a 50 mL round-bottomed flask in ethanol (35 ml) to give a light brown solution. TOSMIC (1.54 g, 7.86 mmol, Eq: 1.2) and potassium carbonate (2.17 g, 15.7 mmol, Eq: 2.4) was successively added, and the reaction mixture was stirred at 70° C. for 3 h when TLC indicated the absence of starting material. The reaction mixture was filtered, washed with EtOH and concentrated i. v. The residue was poured onto 100 mL AcOEt, washed with H$_2$O and brine. The combined organic layers were dried over Na$_2$SO$_4$ and concentrated i. v. Purification by flash chromatography (silica gel, 300 g, AcOEt/heptane=2/1) finally delivered 812 mg of the title compound as white solid. MS (ESI): 276.1, 278.0[M+H]+.

Step 2

3-(3-Chloro-4-cyano-phenyl)-3H-imidazole-4-carboxylic acid methoxy-methyl-amide

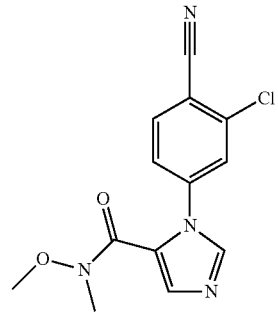 [SMILES: CON(C)C(=O)c1cncn1-c1ccc(C#N)c(Cl)c1]

In a 25 mL three-necked flask, N,O-dimethylhydroxylamine hydrochloride (159 mg, 1.63 mmol, Eq: 3) was combined with DCM (10 ml) to give a white suspension. Dimethylaluminum chloride (1M in hexane, 1.63 ml, 1.63 mmol, Eq: 3) was added at 2-4° C. within 5 min, and the mixture was stirred for 1 h allowing the temperature to rise to rt. A solution of the above prepared 3-(3-chloro-4-cyano-phenyl)-3H-imidazole-4-carboxylic acid ethyl ester (150 mg, 544 μmol, Eq: 1.00) in DCM (5 ml) was then added dropwise, and the reaction allowed to proceed for 17 hr at rt. The reaction was then carefully quenched at 0° C. with sat. NaHCO$_3$ (8 ml), filtered over celite and washed with CH$_2$Cl$_2$. The filtrate was washed with NaHCO$_3$ and brine and the aqueous layers were back-extracted with CH$_2$Cl$_2$. The combined organic layers were dried over Na$_2$SO$_4$ and concentrated i. v. The crude product was then purified by flash chromatography (silica gel, 20 g, 50% to 100% EtOAc in heptane) to give, besides 23 mg of starting material, 96 mf of the title compound as white semisolid. MS (ESI): 291.0, 293.0[M+H]+.

Step 3

2-Chloro-4-[5-(4-chloro-benzoyl)-imidazol-1-yl]-benzonitrile

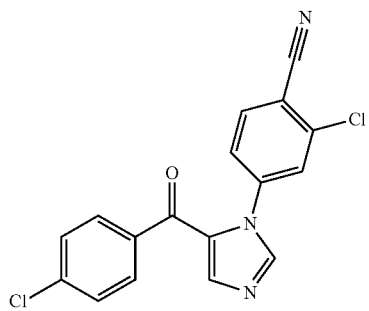 [SMILES: N#Cc1ccc(-n2cncc2C(=O)c2ccc(Cl)cc2)cc1Cl]

The above synthesized 1-(3-chloro-4-cyanophenyl)-N-methoxy-N-methyl-1H-imidazole-5-carboxamide (90 mg, 310 μmol, Eq: 1.00) was dissolved in THF (4 ml) to give a colorless solution. After cooling to 0° C., (4-chlorophenyl)magnesium bromide (1M in Et$_{20}$, 1.08 ml, 1.08 mmol, Eq: 3.5) was added and the reaction mixture was stirred for 10 min at 0° C. and then for 1 h at rt when TLC indicated that the reaction was complete. The reaction was quenched with sat. NH$_4$Cl (5 mL), extracted with EtOAc and washed with NaHCO$_3$. The combined organic layers were washed with brine, dried over Na₂SO₄, and concentrated i. v. Purification by flash chromatography (silica gel, 10 g, 30% to 100% EtOAc in heptane) afforded finally, after trituration with heptane, 77 mg of the title compound as white solid. MS (ESI): 342.0, 343.9[M+H]⁺.

Example 78

2-Chloro-4-[5-(3,4-dichloro-benzoyl)-imidazol-1-yl]-benzonitrile

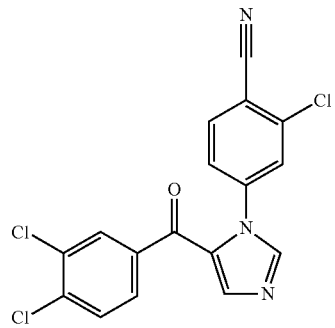 [SMILES: N#Cc1ccc(-n2cncc2C(=O)c2ccc(Cl)c(Cl)c2)cc1Cl]

was prepared in analogy to example 77, but using in step 3 (3,4-dichlorophenyl)magnesium bromide instead of (4-chlorophenyl)magnesium bromide, as white solid. MS (ESI): 375.9, 378.1, 379.9 [M+H]⁺.

Example 79

(3-Methoxy-4-trifluoromethylsulfanyl-phenyl)-(3-methyl-3H-imidazol-4-yl)-methanone

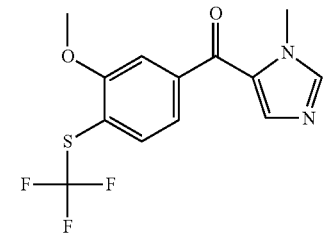 [SMILES: COc1cc(C(=O)c2cncn2C)ccc1SC(F)(F)F]

was prepared in analogy to example 73, but using in step 1 3-methoxy-4-trifluoromethylsulfanyl-benzaldehyde instead of 4-trifluoromethylsulfanyl-benzaldehyde, as colorless oil. MS (ESI): 317.1 [M+H]⁺.

Example 80

(3-Ethyl-3H-imidazol-4-yl)-(3-methoxy-4-trifluoromethylsulfanyl-phenyl)-methanone

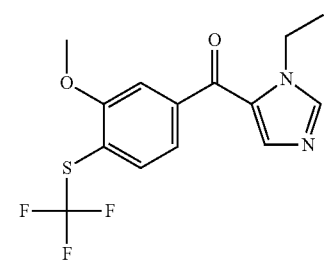 [SMILES: CCn1cncc1C(=O)c1ccc(SC(F)(F)F)c(OC)c1]

was prepared in analogy to example 79, but using in step 1 5-bromo-1-ethyl-1H-imidazole (intermediate 1a') instead of 5-iodo-1-methyl-1H-imidazole, as colorless oil. MS (ESI): 331.1 [M+H]⁺.

Example 81

(3-Isopropyl-3H-imidazol-4-yl)-(3-methoxy-4-trifluoromethylsulfanyl-phenyl)-methanone

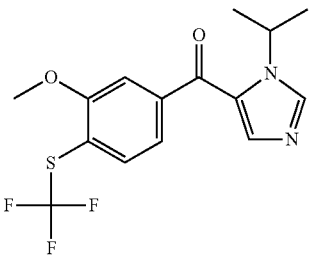 [SMILES: COc1cc(C(=O)c2cncn2C(C)C)ccc1SC(F)(F)F]

was prepared in analogy to example 79, but using in step 1 5-Bromo-1-isopropyl-1H-imidazole (intermediate 1b') instead of 5-iodo-1-methyl-1H-imidazole, as colorless oil. MS (ESI): 345.1 [M+H]⁺.

Example 82

4-[3-(1-Ethyl-propyl)-3H-imidazole-4-carbonyl]-benzonitrile

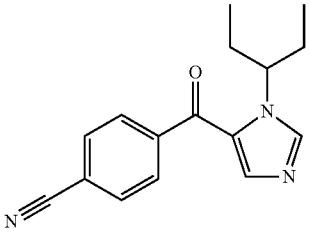 [SMILES: CCC(CC)n1cncc1C(=O)c1ccc(C#N)cc1]

was prepared in analogy to example 2, but starting the sequence with 5-bromo-1-(1-ethyl-propyl)-1H-imidazole (intermediate 1f') instead of 5-iodo-1-methyl-1H-imidazole, as white semisolid. MS (ESI): 268.2 [M+H]⁺.

Example 83

3-[3-(1-Ethyl-propyl)-3H-imidazole-4-carbonyl]-benzonitrile

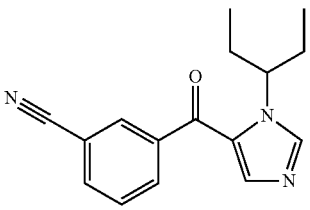 [SMILES: CCC(CC)n1cncc1C(=O)c1cccc(C#N)c1]

was prepared in analogy to example 82, but using in step 1 3-formyl-benzonitrile instead of 4-formyl-benzonitrile, as colorless oil. MS (ESI): 268.2 [M+H]+.

Example 84

[4-(3-Methyl-3H-imidazole-4-carbonyl)-phenyl]-carbamic acid tert-butyl ester

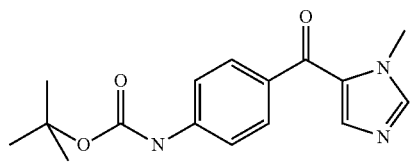 [SMILES: Cn1cncc1C(=O)c1ccc(NC(=O)OC(C)(C)C)cc1]

was synthesized in analogy to example 1, but using in step 1 (4-formyl-phenyl)-carbamic acid tert-butyl ester instead of 4-chlorobenzaldehyde, as yellow oil. MS (ESI): 302.2 [M+H]+.

Example 85

Methyl-[4-(3-methyl-3H-imidazole-4-carbonyl)-phenyl]-carbamic acid tert-butyl ester

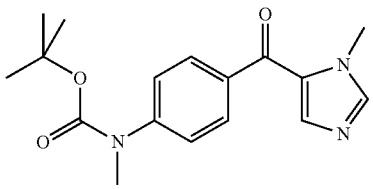 [SMILES: CN(C(=O)OC(C)(C)C)c1ccc(C(=O)c2cncn2C)cc1]

was synthesized in analogy to example 84, but using in step 1 (4-formyl-phenyl)-methyl-carbamic acid tert-butyl ester instead of (4-formyl-phenyl)-carbamic acid tert-butyl ester, as yellow oil. The former aldehyde was prepared from the latter by alkylation with MeI in acetonitrile in the presence of $Cs_2CO_3$ at ambient temperature. MS (ESI): 316.1 [M+H]+.

Example 86

(4-Methylamino-phenyl)-(3-methyl-3H-imidazol-4-yl)-methanone

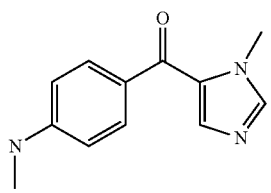 [SMILES: CNc1ccc(C(=O)c2cncn2C)cc1]

The above prepared tert-butyl methyl(4-(1-methyl-1H-imidazole-5-carbonyl)phenyl)carbamate (0.218 g, 691 µmol, Eq: 1.00) was dissolved in DCM (3 ml); HCl in dioxane (4M, 2 ml) was added and the reaction allowed to proceed at RT for 2 additional hours. The mixture was then poured into 5 mL sat. $NaHCO_3$ and extracted with DCM (2×5 mL). The organic layers were combined, washed with brine, dried over $Na_2SO_4$, and concentrated i. v. The crude material was finally purified by flash chromatography (silica gel, 10 g, 5% to 10% MeOH in DCM) to yield 131 mg of the title compound as yellow solid. MS (ESI): 216.2 [M+H]+.

Example 87

N-Methyl-N-[4-(3-methyl-3H-imidazole-4-carbonyl)-phenyl]-formamide

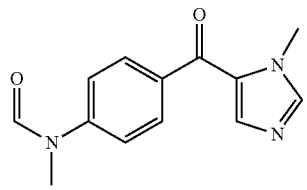 [SMILES: CN(C=O)c1ccc(C(=O)c2cncn2C)cc1]

In a 10 mL pear-shaped flask, formic acid (275 mg, 229 µl, 5.98 mmol, Eq: 11) was combined with acetic anhydride (555 mg, 513 µl, 5.44 mmol, Eq: 10) and the reaction was heated at 55° C. for 1.5 hour (->colorless solution). The above prepared (1-methyl-1H-imidazol-5-yl)(4-(methylamino)phenyl)methanone (0.117 g, 544 µmol, Eq: 1.00), dissolved in DCM (1 ml), was added at RT and the reaction mixture was stirred at ambient temperature overnight. It was quenched by pouring into 2 mL sat. $NaHCO_3$ and extracted with DCM (2×5 mL). The organic layers were combined, washed with brine, dried over $Na_2SO_4$, and concentrated i. v. Purification by flash chromatography (silica gel, 10 g, 5% to 10% MeOH in DCM) produced eventually 109 mg of the title product as white solid. MS (ESI): 244.2 [M+H]+.

Example 88

[4-(3-Ethyl-3H-imidazole-4-carbonyl)-phenyl]-methyl-carbamic acid tert-butyl ester

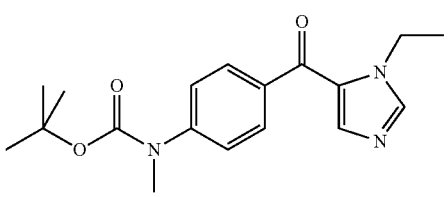 [SMILES: CCn1cncc1C(=O)c1ccc(N(C)C(=O)OC(C)(C)C)cc1]

was synthesized in analogy to example 85, but using as starting component 5-bromo-1-ethyl-1H-imidazole (intermediate 1a') instead of 5-iodo-1-methyl-1H-imidazole, as yellow oil. MS (ESI): 330.2 [M+H]+.

Example 89

N-[4-(3-Ethyl-3H-imidazole-4-carbonyl)-phenyl]-N-methyl-formamide

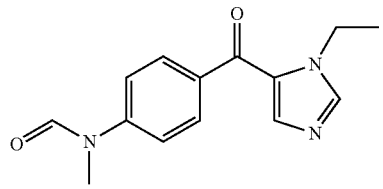 [SMILES: CCn1cncc1C(=O)c1ccc(N(C)C=O)cc1]

was synthesized in analogy to example 87, but using as starting component 5-bromo-1-ethyl-1H-imidazole (intermediate 1a') instead of 5-iodo-1-methyl-1H-imidazole, as white solid. MS (ESI): 258.2 [M+H]$^+$.

Example 90

(4-Chloro-phenyl)-[3-(4-chloro-phenyl)-3H-imidazol-4-yl]-methanone

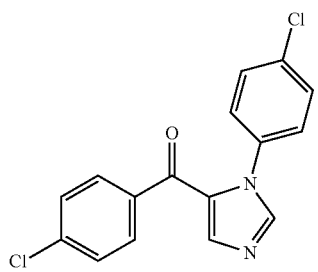 [SMILES: O=C(c1ccc(Cl)cc1)c1cncn1-c1ccc(Cl)cc1]

was prepared in analogy to example 77, but starting the reaction sequence with 4-chloro-phenylamine instead of 4-amino-2-chlorobenzonitrile, as white semisolid. MS (ESI): 317.0, 319.0 [M+H]$^+$.

Example 91

[3-(4-Chloro-phenyl)-3H-imidazol-4-yl]-(3,4-dichloro-phenyl)-methanone

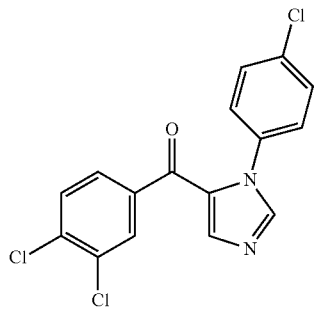 [SMILES: O=C(c1ccc(Cl)c(Cl)c1)c1cncn1-c1ccc(Cl)cc1]

was prepared in analogy to example 90, but using in step 3 (3,4-dichlorophenyl)magnesium bromide instead of (4-chlorophenyl)magnesium bromide, as white solid. MS (ESI): 351.0, 353.1, 355.0 [M+H]$^+$.

Example 92

(4-Chloro-3-fluoro-phenyl)-[3-(4-chloro-phenyl)-3H-imidazol-4-yl]-methanone

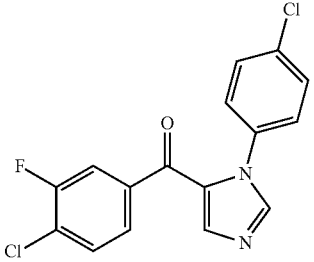 [SMILES: O=C(c1ccc(Cl)c(F)c1)c1cncn1-c1ccc(Cl)cc1]

was prepared in analogy to example 90, but using in step 3 (4-chloro-3-fluorophenyl)magnesium bromide instead of (4-chlorophenyl)magnesium bromide, as white semisolid. MS (ESI): 335.0, 337.0 [M+H]$^+$.

Example 93

N-[4-(3-Isopropyl-3H-imidazole-4-carbonyl)-phenyl]-N-methyl-formamide

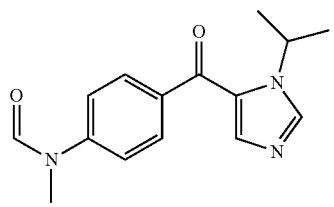 [SMILES: CC(C)n1cncc1C(=O)c1ccc(N(C)C=O)cc1]

was synthesized in analogy to example 87, but using as starting component 5-bromo-1-isopropyl-1H-imidazole (intermediate 1b') instead of 5-iodo-1-methyl-1H-imidazole, as yellow oil. MS (ESI): 272.3 [M+H]$^+$.

Example 94

4-[5-(4-Chloro-3-fluoro-benzoyl)-imidazol-1-yl]-benzonitrile

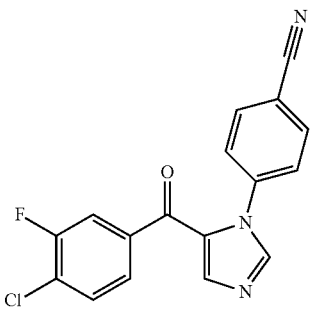 [SMILES: N#Cc1ccc(-n2cncc2C(=O)c2ccc(Cl)c(F)c2)cc1]

was prepared in analogy to example 92, but starting the reaction sequence with 4-amino-benzonitrile instead of 4-chloro-phenylamine, as white solid. MS (ESI): 326.2, 328.0 [M+H]$^+$.

Example 95

4-[5-(4-Chloro-benzoyl)-imidazol-1-yl]-benzonitrile

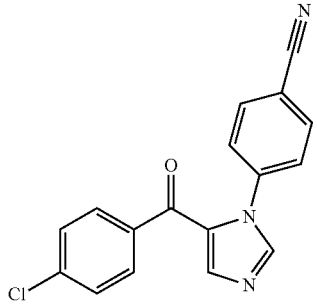 [SMILES: N#Cc1ccc(-n2cncc2C(=O)c2ccc(Cl)cc2)cc1]

was prepared in analogy to example 94, but using in step 3 (4-chlorophenyl)magnesium bromide instead of (4-chloro-3-fluorophenyl)magnesium bromide, as white solid. MS (ESI): 308.1, 310.2 [M+H]$^+$.

Example 96

4-[5-(3,4-Dichloro-benzoyl)-imidazol-1-yl]-benzonitrile

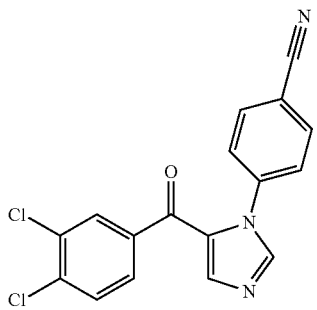 [SMILES: N#Cc1ccc(-n2cncc2C(=O)c2ccc(Cl)c(Cl)c2)cc1]

was prepared in analogy to example 94, but using in step 3 (3,4-dichlorophenyl)-magnesium bromide instead of (4-chloro-3-fluorophenyl)magnesium bromide, as white solid. MS (ESI): 342.0, 344.0 [M+H]$^+$.

Example 97

[3-(4-Chloro-phenyl)-3H-imidazol-4-yl]-(3,4-difluoro-phenyl)-methanone

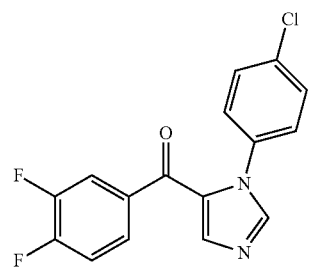 [SMILES: O=C(c1ccc(F)c(F)c1)c1cncn1-c1ccc(Cl)cc1]

was prepared in analogy to example 92, but using in step 3 (3,4-difluorophenyl)magnesium bromide instead of (4-chloro-3-fluorophenyl)magnesium bromide, as white semisolid. MS (ESI): 319.0, 321.1 [M+H]$^+$.

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A Compound of formula (I)

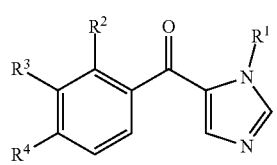

wherein

R$^1$ is methyl, ethyl, isopropyl, pentan-3-yl or cyanophenyl;

R$^2$ is H, halogen, cyano, nitro, alkyl, haloalkyl, cycloalkyl, halocycloalkyl, cycloalkylalkyl, halocycloalkylalkyl, alkoxy, haloalkoxy, alkoxyalkyl, haloalkoxyalkyl, cycloalkoxy, halocycloalkoxy or hydroxyalkyl;

R$^3$ is H, chloro, fluoro, cyano, or methoxy;

R$^4$ is H, halogen, cyano, nitro, substituted amino, alkyl, cycloalkyl, halocycloalkyl, cycloalkyl alkyl, halocycloalkylalkyl, alkynyl, alkoxy, haloalkoxy, alkylsulfanyl, cycloalkylsulfanyl, haloalkylsulfanyl, alkylsulfonyl, cycloalkylsulfonyl, haloalkylsulfonyl, alkoxyalkyl, haloalkoxyalkyl, cycloalkoxy, halocycloalkoxy or hydroxyalkyl, wherein substituted amino is substituted with R$^8$ and R$^9$;

or $R^3$ and $R^4$ together form —CH$_2$—CH$_2$—C(O)—N(CH$_3$)— or —CH=CH—S—

$R^5$, $R^6$ and $R^7$ are independently selected from H, halogen, cyano, alkyl, haloalkyl, cycloalkyl, halocycloalkyl, cycloalkylalkyl, halocycloalkyl alkyl, alkoxy, haloalkoxy, alkoxyalkyl, haloalkoxyalkyl, cycloalkoxy, halocycloalkoxy and hydroxyalkyl;

$R^8$ is alkyl, cycloalkyl, formyl, alkylcarbonyl or alkoxycarbonyl;

$R^9$ is H, alkyl or cycloalkyl;

or a pharmaceutically acceptable salt thereof;

with the proviso that at least one of $R^2$, $R^3$ and $R^4$ is different from H and that (4-chlorophenyl)(1-methyl-1H-imidazol-5-yl)-methanone, 2-fluoro-4-[(1-methyl-1H-imidazol-5-yl)carbonyl]-benzonitrile, 4-[(1-methyl-1H-imidazol-5-yl)carbonyl]-benzonitrile, 2-bromo-4-[(1-methyl-1H-imidazol-5-yl)carbonyl]-benzonitrile, (4-chlorophenyl)[1-(1-methyl ethyl)-1H-imidazol-5-yl]-methanone, [4-(1-methyl ethyl)phenyl](1-methyl-1H-imidazol-5-yl)-methanone, (4-ethylphenyl)(1-methyl-1H-imidazol-5-yl)-methanone, (1-methyl-1H-imidazol-5-yl)(4-methylphenyl)-methanone, (4-chlorophenyl)(1-ethyl-1H-imidazol-5-yl)-methanone, (4-chloro-3-methylphenyl)(1-methyl-1H-imidazol-5-yl)methanone, (1-methyl-1H-imidazol-5-yl)[3-(trifluoromethyl)phenyl]-methanone, (4-chloro-2-fluoro-5-methoxyphenyl)(1-methyl-1H-imidazol-5-yl)-methanone, (2-fluorophenyl)(1-methyl-1H-imidazol-5-yl)-methanone, and (3-bromophenyl)(1-methyl-1H-imidazol-5-yl)-methanone are excluded.

2. A compound according to claim 1, wherein $R^2$ is H or halogen.

3. A compound according to claim 1, wherein $R^2$ is H, chloro or fluoro.

4. A compound according to claim 1, wherein $R^2$ is H.

5. A compound according to claim 1, wherein $R^3$ is H, chloro or methoxy.

6. A compound according to claim 1, wherein $R^4$ is H, halogen, cyano, substituted amino, alkyl, alkynyl, alkoxy, alkylsulfanyl, haloalkylsulfanyl or alkylsulfonyl, wherein substituted amino is substituted with $R^8$ and $R^9$.

7. A compound according to claim 1, wherein $R^4$ is halogen, cyano, substituted amino or alkylsulfanyl, wherein substituted amino is substituted with with $R^8$ and $R^9$.

8. A compound according to claim 1, wherein $R^4$ is halogen, cyano, substituted amino or alkylsulfanyl, wherein substituted amino is substituted with formyl and alkyl.

9. A compound according to claim 1, wherein $R^3$ and $R^4$ together form —CH$_2$—CH$_2$—C(O)—N(CH$_3$)— or —CH=CH—S—.

10. A compound according to claim 1, wherein $R^3$ and $R^4$ together form —CH$_2$—CH$_2$—C(O)—N(CH$_3$)—.

11. A compound according to claim 1, wherein $R^5$, $R^6$ and $R^7$ are independently selected from H, halogen or cyano.

12. A compound according to claim 1, wherein $R^8$ is alkyl, formyl, alkylcarbonyl or alkoxycarbonyl.

13. A compound according to claim 1, wherein $R^8$ is formyl.

14. A compound according to claim 1, wherein $R^9$ is H or alkyl.

15. A compound according to claim 1, wherein $R^9$ is alkyl.

16. A compound according to claim 1, wherein $R^9$ is methyl.

17. A compound of claim 1 selected from
(3,4-dichlorophenyl)(1-methyl-1H-imidazol-5-yl)methanone;
4-(1-ethyl-1H-imidazole-5-carbonyl)benzonitrile;
1-methyl-6-(1-methyl-1H-imidazole-5-carbonyl)-3,4-dihydroquinolin-2(1H)-one;
6-(1-ethyl-1H-imidazole-5-carbonyl)-1-methyl-3,4-dihydroquinolin-2(1H)-one;
(1-methyl-1H-imidazol-5-yl)(4-(methylthio)phenyl)methanone;
2-chloro-4-(isopropyl-1H-imidazole-5-carbonyl)benzonitrile;
(3-methoxy-4-(trifluoromethylthio)phenyl)(1-methyl-1H-imidazol-5-yl)methanone;
4-(1-(pentan-3-yl)-1H-imidazole-5-carbonyl)benzonitrile;
N-(4-(1-ethyl-1H-imidazole-5-carbonyl)phenyl)-N-methylformamide; and
4-(5-(4-chlorobenzoyl)-1H-imidazol-1-yl)benzonitrile;
and pharmaceutically acceptable salts thereof.

* * * * *